US011920174B2

(12) United States Patent
Eber et al.

(10) Patent No.: US 11,920,174 B2
(45) Date of Patent: Mar. 5, 2024

(54) RNA ANALYSIS BY TOTAL HYDROLYSIS AND QUANTIFICATION OF RELEASED NUCLEOSIDES

(71) Applicant: CureVac SE, Tübingen (DE)

(72) Inventors: Fabian Johannes Eber, Tübingen (DE); Aniela Wochner, Tübingen (DE); Tilmann Roos, Kusterdingen (DE)

(73) Assignee: CureVac SE, Tübingen (DE)

( * ) Notice: Subject to any disclaimer, the term of this patent is extended or adjusted under 35 U.S.C. 154(b) by 1523 days.

(21) Appl. No.: 16/081,863

(22) PCT Filed: Mar. 3, 2017

(86) PCT No.: PCT/EP2017/055048
§ 371 (c)(1),
(2) Date: Aug. 31, 2018

(87) PCT Pub. No.: WO2017/149139
PCT Pub. Date: Sep. 8, 2017

(65) Prior Publication Data
US 2019/0100784 A1 Apr. 4, 2019

(30) Foreign Application Priority Data

Mar. 3, 2016 (WO) ................ PCT/EP2016/054599

(51) Int. Cl.
*C12P 19/34* (2006.01)
*C12N 9/22* (2006.01)
*C12Q 1/6806* (2018.01)
*C12Q 1/6809* (2018.01)
*C12Q 1/6869* (2018.01)
*G16B 30/00* (2019.01)

(52) U.S. Cl.
CPC .............. *C12P 19/34* (2013.01); *C12N 9/22* (2013.01); *C12Q 1/6806* (2013.01); *C12Q 1/6809* (2013.01); *G16B 30/00* (2019.02); *C12Q 1/6869* (2013.01); *C12Y 301/03001* (2013.01); *C12Y 301/04001* (2013.01); *C12Y 301/26005* (2013.01)

(58) Field of Classification Search
None
See application file for complete search history.

(56) References Cited

U.S. PATENT DOCUMENTS

| 7,074,596 | B2 | 7/2006 | Darzynkiewicz et al. |
|---|---|---|---|
| 2005/0032730 | A1 | 2/2005 | von der Mülbe et al. |
| 2005/0059624 | A1 | 3/2005 | Hoerr et al. |
| 2005/0250723 | A1 | 11/2005 | Hoerr et al. |
| 2006/0188490 | A1 | 8/2006 | Hoerr et al. |
| 2006/0275747 | A1 | 12/2006 | Hardy et al. |
| 2008/0025944 | A1 | 1/2008 | Hoerr et al. |
| 2008/0267873 | A1 | 10/2008 | Hoerr et al. |
| 2009/0324584 | A1 | 12/2009 | Hoerr et al. |
| 2010/0048883 | A1 | 2/2010 | Ketterer et al. |
| 2010/0189729 | A1 | 7/2010 | Hoerr et al. |
| 2010/0203076 | A1 | 8/2010 | Fotin-Mleczek et al. |
| 2010/0291156 | A1 | 11/2010 | Barner et al. |
| 2010/0305196 | A1 | 12/2010 | Probst et al. |
| 2011/0053829 | A1 | 3/2011 | Baumhof et al. |
| 2011/0250225 | A1 | 10/2011 | Fotin-Mleczek et al. |
| 2012/0021043 | A1 | 1/2012 | Kramps et al. |
| 2012/0258046 | A1 | 10/2012 | Mutzke |
| 2013/0129754 | A1 | 5/2013 | Thess et al. |
| 2013/0142818 | A1 | 6/2013 | Baumhof et al. |
| 2013/0259879 | A1 | 10/2013 | Baumhof et al. |
| 2013/0280283 | A1 | 10/2013 | Lorenz et al. |
| 2013/0295043 | A1 | 11/2013 | Kallen et al. |
| 2013/0336998 | A1 | 12/2013 | Kallen et al. |
| 2015/0037326 | A1 | 2/2015 | Butler-Ransohoff et al. |
| 2015/0050302 | A1 | 2/2015 | Thess |
| 2015/0057340 | A1 | 2/2015 | Thess et al. |
| 2015/0093413 | A1 | 4/2015 | Thess et al. |
| 2015/0118183 | A1 | 4/2015 | Baumhof |
| 2015/0118264 | A1 | 4/2015 | Baumhof et al. |
| 2015/0165006 | A1 | 6/2015 | Thess et al. |
| 2015/0184195 | A1 | 7/2015 | Thess et al. |
| 2015/0218554 | A1 | 8/2015 | Thess |
| 2015/0306249 | A1 | 10/2015 | Baumhof et al. |
| 2015/0320847 | A1 | 11/2015 | Thess et al. |
| 2016/0024493 | A1 | 1/2016 | Robins |
| 2016/0046949 | A1* | 2/2016 | May .................... A61K 38/465 536/23.2 |
| 2016/0130345 | A1 | 5/2016 | Fotin-Mleczek et al. |
| 2016/0166668 | A1 | 6/2016 | Kallen et al. |
| 2016/0166678 | A1 | 6/2016 | Kallen et al. |
| 2016/0166710 | A1 | 6/2016 | Baumhof |
| 2016/0166711 | A1 | 6/2016 | Schnee et al. |
| 2016/0168207 | A1 | 6/2016 | Kramps et al. |
| 2016/0168227 | A1 | 6/2016 | Kallen et al. |
| 2016/0235864 | A1 | 8/2016 | Schlake et al. |
| 2016/0304883 | A1 | 10/2016 | Grund et al. |
| 2016/0304938 | A1 | 10/2016 | Wochner |
| 2016/0326575 | A1 | 11/2016 | von der Mülbe |
| 2016/0331844 | A1 | 11/2016 | Fotin-Mleczek et al. |
| 2017/0014496 | A1 | 1/2017 | Fotin-Mleczek et al. |
| 2017/0029847 | A1 | 2/2017 | Thess |
| 2017/0114378 | A1 | 4/2017 | Wochner et al. |
| 2017/0183700 | A1 | 6/2017 | Hamana et al. |

(Continued)

FOREIGN PATENT DOCUMENTS

| EP | 1518928 | 3/2005 |
|---|---|---|
| EP | 2742951 | 6/2014 |

(Continued)

OTHER PUBLICATIONS

Andrus et al., "Base Composition Analysis of Nucleosides Using HPLC", In: *Current Protocols in Nucleic Acid Chemistry*, John Wiley & Sons, Inc., pp. 10.6.1-10.6.6, 2001.

(Continued)

*Primary Examiner* — Christian L Fronda
(74) *Attorney, Agent, or Firm* — Parker Highlander PLLC

(57) ABSTRACT

The present invention relates to analysis of an RNA molecule. It further relates to the use of this method for the quality control of an RNA molecule produced by in vitro transcription or for the quality control of an RNA molecule produced by chemical synthesis.

20 Claims, 4 Drawing Sheets

Specification includes a Sequence Listing.

(56) References Cited

U.S. PATENT DOCUMENTS

| | | |
|---|---|---|
| 2017/0252430 A1 | 9/2017 | Fotin-Mleczek et al. |
| 2017/0326225 A1 | 11/2017 | Rauch et al. |
| 2018/0044687 A1 | 2/2018 | Thess et al. |
| 2018/0066325 A1 | 3/2018 | Kelleher et al. |
| 2018/0125952 A1 | 5/2018 | Fotin-Mleczek et al. |
| 2018/0126003 A1 | 5/2018 | Hoerr |
| 2018/0142275 A1 | 5/2018 | Roos et al. |
| 2018/0147146 A1 | 5/2018 | Eber et al. |
| 2018/0148727 A1 | 5/2018 | Grund et al. |
| 2018/0201967 A1 | 7/2018 | Eber et al. |
| 2018/0208957 A1 | 7/2018 | Roos et al. |
| 2018/0214537 A1 | 8/2018 | Mutzke et al. |
| 2018/0237786 A1 | 8/2018 | Schlake et al. |
| 2018/0237817 A1 | 8/2018 | Roos et al. |
| 2018/0243219 A1 | 8/2018 | Ketterer et al. |
| 2018/0296663 A1 | 10/2018 | Hipp et al. |
| 2018/0298372 A1 | 10/2018 | Funkner et al. |
| 2018/0312545 A1 | 11/2018 | Baumhof et al. |
| 2018/0371392 A1 | 12/2018 | Mayer et al. |
| 2019/0010485 A1 | 1/2019 | Yazdan Panah et al. |
| 2019/0017100 A1 | 1/2019 | Wochner et al. |
| 2019/0024096 A1 | 1/2019 | Schmid et al. |
| 2019/0040378 A1 | 2/2019 | Fotin-Mleczek et al. |
| 2019/0049414 A1 | 2/2019 | Wochner et al. |
| 2019/0083602 A1 | 3/2019 | Roos et al. |
| 2019/0100784 A1 | 4/2019 | Eber et al. |
| 2019/0125857 A1 | 5/2019 | Rauch et al. |
| 2019/0133950 A1 | 5/2019 | Eber et al. |
| 2019/0160164 A1 | 5/2019 | Rauch et al. |
| 2019/0177714 A1 | 6/2019 | Kunze et al. |
| 2019/0185859 A1 | 6/2019 | Fotin-Mleczek et al. |
| 2019/0194760 A1 | 6/2019 | Koch et al. |
| 2019/0225971 A1 | 7/2019 | Williams |
| 2019/0241633 A1 | 8/2019 | Fotin-Mleczek et al. |
| 2019/0249219 A1 | 8/2019 | Reichert et al. |
| 2019/0336608 A1 | 11/2019 | Baumhof et al. |
| 2019/0336611 A1 | 11/2019 | Baumhof et al. |
| 2019/0343933 A1 | 11/2019 | Horscroft et al. |
| 2019/0343942 A1 | 11/2019 | Fotin-Mleczek et al. |
| 2019/0351044 A1 | 11/2019 | Jasny et al. |
| 2019/0351047 A1 | 11/2019 | Jasny et al. |
| 2019/0351048 A1 | 11/2019 | Rauch |
| 2019/0381180 A1 | 12/2019 | Baumhof et al. |
| 2020/0023076 A1 | 1/2020 | Fotin-Mleczek et al. |
| 2020/0085852 A1 | 3/2020 | Fotin-Mleczek |
| 2020/0085944 A1 | 3/2020 | Heidenreich et al. |
| 2020/0149026 A1 | 5/2020 | Horscroft et al. |
| 2020/0163878 A1 | 5/2020 | Baumhof et al. |
| 2020/0179526 A1 | 6/2020 | Baumhof et al. |
| 2020/0318097 A1 | 10/2020 | Funkner et al. |
| 2020/0392572 A1 | 12/2020 | Yazdan Panah et al. |
| 2021/0030864 A1 | 2/2021 | Petsch et al. |
| 2021/0069315 A1 | 3/2021 | Baumhof et al. |
| 2021/0162037 A1 | 6/2021 | Jasny et al. |
| 2021/0170017 A1 | 6/2021 | Lutz et al. |
| 2021/0180106 A1 | 6/2021 | Wochner et al. |
| 2021/0205434 A1 | 7/2021 | Petsch et al. |
| 2021/0260178 A1 | 8/2021 | Jasny et al. |
| 2021/0261897 A1 | 8/2021 | Yazdan Panah et al. |
| 2021/0361761 A1 | 11/2021 | Lutz et al. |
| 2021/0379181 A1 | 12/2021 | Rauch et al. |
| 2021/0403925 A1 | 12/2021 | Chevessier-Tünnesen et al. |
| 2022/0040281 A1 | 2/2022 | Schwendt et al. |
| 2022/0073962 A1 | 3/2022 | Schwenger et al. |
| 2022/0133908 A1 | 5/2022 | Rejman et al. |
| 2022/0144877 A1 | 5/2022 | Heinz et al. |
| 2022/0211838 A1 | 7/2022 | Oostvogels et al. |
| 2022/0233568 A1 | 7/2022 | Schlake et al. |
| 2022/0296628 A1 | 9/2022 | Thess et al. |
| 2022/0313813 A1 | 10/2022 | Rauch et al. |
| 2022/0340641 A1 | 10/2022 | Aggarwal et al. |
| 2023/0064106 A1 | 3/2023 | Heinz et al. |

FOREIGN PATENT DOCUMENTS

| | | |
|---|---|---|
| WO | WO 2002/098443 | 12/2002 |
| WO | WO 2008/016473 | 2/2008 |
| WO | WO 2008/077592 | 7/2008 |
| WO | WO 2008/157688 | 12/2008 |
| WO | WO 2009/149253 | 12/2009 |
| WO | WO 2010/093820 | 8/2010 |
| WO | WO 2010/123501 | 10/2010 |
| WO | WO 2011/015347 | 2/2011 |
| WO | WO 2012/019630 | 2/2012 |
| WO | WO 2012/019780 | 2/2012 |
| WO | WO 2012/104360 | 8/2012 |
| WO | WO 2012/135805 | 10/2012 |
| WO | WO 2013/049231 | 4/2013 |
| WO | WO 2013/052523 | 4/2013 |
| WO | WO 2013/059475 | 4/2013 |
| WO | WO 2013/143700 | 10/2013 |
| WO | WO 2014/005038 | 1/2014 |
| WO | WO 2014/152659 | 9/2014 |
| WO | WO 2015/001416 | 1/2015 |
| WO | WO 2016/184576 | 11/2016 |
| WO | WO 2017/001058 | 1/2017 |
| WO | WO 2017/021546 | 2/2017 |
| WO | WO 2017/025447 | 2/2017 |
| WO | WO 2017/064146 | 4/2017 |
| WO | WO 2017/081110 | 5/2017 |
| WO | WO 2017/098468 | 6/2017 |
| WO | WO 2017/109134 | 6/2017 |
| WO | WO 2017/137095 | 8/2017 |
| WO | WO 2017/140345 | 8/2017 |
| WO | WO 2017/140905 | 8/2017 |
| WO | WO 2017/149139 | 9/2017 |
| WO | WO 2017/162297 | 9/2017 |
| WO | WO 2017/182634 | 10/2017 |
| WO | WO 2017/186928 | 11/2017 |
| WO | WO 2017/191258 | 11/2017 |
| WO | WO 2017/191264 | 11/2017 |
| WO | WO 2017/191274 | 11/2017 |
| WO | WO 2017/203008 | 11/2017 |
| WO | WO 2017/212006 | 12/2017 |
| WO | WO 2017/212007 | 12/2017 |
| WO | WO 2017/212008 | 12/2017 |
| WO | WO 2017/212009 | 12/2017 |
| WO | WO 2018/078053 | 5/2018 |
| WO | WO 2018/096179 | 5/2018 |
| WO | WO 2018/104540 | 6/2018 |
| WO | WO 2018/167320 | 9/2018 |
| WO | WO 2018/172556 | 9/2018 |
| WO | WO 2018/211038 | 11/2018 |
| WO | WO 2019/008001 | 1/2019 |
| WO | WO 2021/123332 | 6/2021 |
| WO | WO 2021/254593 | 12/2021 |
| WO | WO 2022/023559 | 2/2022 |
| WO | WO 2022/043551 | 3/2022 |
| WO | WO 2022/049093 | 3/2022 |

OTHER PUBLICATIONS

Brunelle et al., "In vitro transcription from plasmid or PCR-amplified DNA", *Methods Enzymol.*, 530:101-114, 2013.

Cohen et al., "High-performance capillary electrophoretic separation of bases, nucleosides, and oligonucleotides: retention manipulation via micellar solutions and metal additives", *Anal. Chem.*, 59(7):1021-1027, 1987.

Eadie et al., "High-performance liquid chromatographic analysis of oligodeoxyribonucleotide base composition", *Anal. Biochem.*, 165(2):442-447, 1987.

Fotin-Mleczek et al., "Highly potent mRNA based cancer vaccines represent an attractive platform for combination therapies supporting an improved therapeutic effect", *J. Gene Med.*, 14(6):428-439, 2012.

Geall et al., "RNA: the new revolution in nucleic acid vaccines", *Semin. Immunol.*, 25(2):152-159, 2013.

International Search Report and Written Opinion issued in corresponding PCT Application No. PCT/EP2017/055048, dated May 16, 2017.

(56) References Cited

OTHER PUBLICATIONS

Johnsen et al., "Hydrophilic interaction chromatography of nucleoside triphosphates with temperature as a separation parameter", *J. Chromatogr. A*, 1218(35):5981-5986, 2011.
Kamiya et al., "Mutagenic properties of oxidized GTP and ATP in in vitro transcription-reverse transcription", *Nucleic Acid Symposium Series*, 50:99-100, 2006.
Kammerer et al., "MALDI-TOF MS analysis of urinary nucleosides", *J. Am. Soc. Mass Spectrom.*, 16(6):940-947, 2005.
Kore et al., "Synthesis and biological validation of N7-(4-chlorophenoxyethyl) substituted dinucleotide cap analogs for mRNA translation", *Bioorg. Med. Chem.*, 21(15):4570-4574, 2013.
Li et al., "Development of an isocratic HPLC method for catechin quantification and its application to formulation studies", *Fitoterapia*, 83:1267-1274, 2012.
Nees et al., "Detection of RNA Modifications by HPLC Analysis and Competitive ELISA", In: *Innate DNA and RNA Recognition*, Anders and Migliorni (eds), 1169:3-14, 2014.
Nunomura et al., "Oxidative damage to RNA in aging and neurodegenerative disorders", *Neurotox. Res.*, 22:231-248, 2012.
Shan et al., "Messenger RNA oxidation is an early event preceding cell death and causes reduced protein expression", *FASEB J.*, 21:2753-2764, 2007.
Shimelis et al., "Nuclease P1 digestion/high-performance liquid chromatography, a practical method for DNA quantitation",*J. Chromatog.*, 1117(2):132-136, 2006.
Stepinski et al., "Synthesis and properties of mRNAs containing the novel "anti-reverse" cap analogs 7-methyl(3'-O-methyl)GpppG and 7-methyl(3'-deoxy)GpppG", *RNA*, 7(10):1486-1495, 2001.
Su et al., "Quantitative analysis of ribonucleoside modifications in tRNA by HPLC-coupled mass spectrometry", *Nature Protoc.*, 9(4):828-841, 2014.
Tanaka et al., "RNA oxidation catalyzed by cytochrome c leads to its depurination and cross-linking, which may facilitate cytochrome c release from mitochondria", *Free Radic. Biol. Med.*, 53(4):854-862, 2012.
Theus and Liarakos, "A simple assay for determining the capping efficiencies of RNA polymerases used for in vitro transcription", *BioTechniques*, 9(5):610-615, 1990.
Wietstock, "DNA Composition Analysis by Nuclease Digestion and HPLC", *J. Chem. Ed.*, 72(10):950, 1995.
Boyle et al., "Evaluation of the impact of single nucleotide polymorphisms and primer mismatches on quantitative PCR," BMC Biotechnology, 9:75, 2009.

Danneberg et al., "Sequence-specific RNA cleavage by PNA conjugates of the metal-free artificial ribonuclease tris(2-aminobenzimidazole)," *Beilstein Journal of Organic Chemistry*, 11:493-498, 2015.
Desai and Shankar, "Single-strand-specific nucleases", *FEMS Microbiol. Rev.*, 26:457-491, 2003.
Dogandzhiyski et al., "Studies on Tris(2-aminobenzimidazole)-PNA Based Artificial Nucleases: A Comparison of Two Analytical Techniques," *Bioconjugate Chemistry*, 26(12):2514-2519, 2015.
Dougherty et al., "Quantitative analysis of deadenylation-independent mRNA decay as a modified MBRACE assay," Methods Mol. Biol., 1125:353-371, 2014.
Heighway et al., "Coamplification in tumors of kras2, type 2 inositol 1,4,5 triphosphate receptor gene, and a novel human gene, krag", *Genomics*, 35(1):207-214, 1996.
Kolpashchikov, "An elegant biosensor molecular beacon probe: challenges and recent solutions", *Scientifica*, 928783:1-17, 2012.
Kuzuya et al., "Selective activation of two sites in RNA by acridine-bearing oligonucleotides for clipping of designated RNA fragments," *Journal of the American Chemical Society*, 126(5):1430-1436, 2004.
Li et al., "Ultrasensitive optical DNA biosensor based on surface immobilization of molecular beacon by a bridge structure", *Anal. Sci.*, 17: 1149-1153, 2001.
Maxwell et al., "Assay of DNA-RNA hybrids by S 1 nuclease digestion and adsorption to DEAE-cellulose filters", *Nucl. Acids. Res.*, 5(6):2033-2038, 1978.
Nakanishi et al., "Hair roots as an mRNA source for mutation analysis of Usher syndrome-causing genes," J Hum Genet., 55:701-703, 2010.
Thompson and Sommercorn, "Use of a multiple S1 nuclease protection assay to monitor changes in RNA levels for type 1 phosphatase and several proto-oncogenes in response to insulin", *J. Biol. Chem.*, 267(9):5921-5926, 1992.
Vet and Marras, "Design and optimization of molecular beacon real-time polymerase chain reaction assays", In: *Oligonucleotide Synthesis*, Herdewijn, P. (ed.), 288:273-290, 2005.
Vet et al., "Multiplex detection of four pathogenic retroviruses using molecular beacons", *Proc. Natl. Acad. Sci. USA*, 96:6394-6399, 1999.
Wong and Medrano, "Real-time PCR for mRNA quantitation", *Biotechniques*, 39(1):75-85, 2005.
Zuker, "Mfold web server for nucleic acid folding and hybridization prediction", *Nucl. Acids Res.*, 31(13):3406-3415, 2003.

\* cited by examiner

SEQUENCE LISTING

```
<160> NUMBER OF SEQ ID NOS: 5

<210> SEQ ID NO 1
<211> LENGTH: 1870
<212> TYPE: RNA
<213> ORGANISM: Artificial Sequence
<220> FEATURE:
<223> OTHER INFORMATION: GC-optimized Photinus pyralis sequence

<400> SEQUENCE: 1
gggagaaagc uuaccaugga ggacgccaag aacaucaaga agggcccggc gcccuucuac      60
ccgcuggagg acgggaccgc cggcgagcag cuccacaagg ccaugaagcg guacgcccug     120
gugccgggca cgaucgccuu caccgacgcc cacaucgagg ucgacaucac cuacgcggag     180
uacuucgaga ugagcgugcg ccuggccgag gccaugaagc gguacggccu gaacaccaac     240
caccggaucg ugguugcuc ggagaacagc cugcaguucu ucaugccggu gcugggcgcc     300
cucuucaucg gcguggccgu cgccccggcg aacgacaucu acaacgagcg ggagcugcug     360
aacagcaugg ggaucagcca gccgaccgug guguucguga gcaagaaggg ccugcagaag     420
auccugaacg ugcagaagaa gcugcccauc auccagaaga ucaucaucau ggacagcaag     480
accgacuacc agggcuucca gucgauguac acguucguga ccagccaccu cccgccgggc     540
uucaacgagu acgacuucgu cccggagagc uucgaccggg acaagaccau cgcccugauc     600
augaacagca gcggcagcac cggccugccg aaggggugg cccugccgca ccggaccgcc     660
ugcgugcgcu ucucgcacgc ccgggacccc aucuucggca accagaucau cccggacacc     720
gccauccuga gcgugguugcc guuccaccac ggcuucggca uguucacgac ccugggcuac     780
cucaucugcg gcuuccgggu gguccugaug uaccgguucg aggaggagcu guuccugcgg     840
agccugcagg acuacaagau ccagagcgcg cugcucuguc cgacccuguu cagcuucuuc     900
gccaagagca cccugaucga caaguacgac cugucgaacc ugcacgagau cgccagcggg     960
```

| | |
|---|---|
| ggcgccccgc ugagcaagga ggugggcgag gccguggcca agcgguucca ccucccgggc | 1020 |
| auccgccagg gcuacggccu gaccgagacc acgagcgcga uccugaucac ccccgagggg | 1080 |
| gacgacaagc cgggcgccgu gggcaaggug gucccguucu cgaggccaa ggugguggac | 1140 |
| cuggacaccg gcaagacccu gggcgugaac cagcggggcg agcugugcgu gcgggggccg | 1200 |
| augaucauga gcggcuacgu gaacaacccg gaggccacca acgcccucau cgacaaggac | 1260 |
| ggcuggcugc acagcggcga caucgccuac ugggacgagg acgagcacuu cuucaucguc | 1320 |
| gaccggcuga agucgcugau caaguacaag ggcuaccagg uggcgccggc cgagcuggag | 1380 |
| agcauccugc uccagcaccc caacaucuuc gacgccggcg uggccgggcu gccggacgac | 1440 |
| gacgccggcg agcugccggc cgcgguggug ugcuggagc acggcaagac caugacggag | 1500 |
| aaggagaucg ucgacuacgu ggccagccag gugaccaccg ccaagaagcu gcggggcggc | 1560 |
| gugguguucg uggacgaggu cccgaagggc cugaccggga agcucgacgc ccggaagauc | 1620 |
| cgcgagaucc ugaucaaggc caagaagggc ggcaagaucg ccgugugagg acuaguuaua | 1680 |
| agacugacua gcccgauggg ccucccaacg ggccccccuc cccuccuugc accgagauua | 1740 |
| auaaaaaaaa aaaaaaaaaa aaaaaaaaaa aaaaaaaaaa aaaaaaaaaa aaaaaaaaaa | 1800 |
| aaaaaaugca ucccccccc cccccccccc ccccccccccc ccaaaggcuc uuucagagc | 1860 |
| caccagaauu | 1870 |

<210> SEQ ID NO 2
<211> LENGTH: 589
<212> TYPE: RNA
<213> ORGANISM: Artificial Sequence
<220> FEATURE:
<223> OTHER INFORMATION: GC-optimized human cancer antigen mRNA

<400> SEQUENCE: 2

| | |
|---|---|
| gggagaaagc uuaccaugaa ggccgugcug cucgcgcugc ugauggccgg ccuggcccug | 60 |
| cagccgggga ccgcccugcu gugcuacagc ugcaaggccc aggucucgaa cgaggacugc | 120 |
| cugcagguug agaacugcac gcagcugggc gagcagugcu ggaccgcccg gauccgcgcc | 180 |
| gugggccuc ucaccgugau cagcaagggc ugcagccuga acugcgugga cgacagccag | 240 |
| gacuacuacg ugggcaagaa gaacaucacc ugcugcgaca ccgaccugug caacgccagc | 300 |
| ggcgcccacg cccugcagcc gcggccgccc auccuggccc ugcugccgc ccugggccug | 360 |
| cugcucuggg gccccggcca gcugugacca cuaguuauaa gacugacuag cccgaugggc | 420 |
| cucccaacgg gccuccucc ccuccuugca ccgagauuaa uaaaaaaaa aaaaaaaaaa | 480 |
| aaaaaaaaaa aaaaaaaaaa aaaaaaaaaa aaaaaaaaaa aaaaaugcau ccccccccc | 540 |
| ccccccccc ccccccccc caaaggcucu uuucagagcc accagaauu | 589 |

<210> SEQ ID NO 3
<211> LENGTH: 760
<212> TYPE: RNA
<213> ORGANISM: Artificial Sequence
<220> FEATURE:
<223> OTHER INFORMATION: GC-optimized human cancer antigen mRNA

<400> SEQUENCE: 3

| | |
|---|---|
| gggagaaagc uuaccaugca ggccgagggc cgcggcaccg gcggcucgac cggcgacgcc | 60 |
| gacgggcccg gcgggcccgg gcauccggac ggcccggggcg ggaacgcggg cggcccgggc | 120 |
| gaggccggcg ccaccggcgg gcggggcccg cggggcgccg gcgccgcccg ggcgagcggc | 180 |
| cccggcgggg gcgccccgcg gggcccgcac ggcggcgccg ccagcggccu gaacgggguc | 240 |

| | |
|---|---|
| ugccggugcg gcgcccgcgg cccggagagc cggcuccugg aguucuaccu ggccaugccg | 300 |
| uucgcgaccc cgauggaggc cgagcuggcc cggcggagcc uggcccagga cgccccgccg | 360 |
| cugcccgugc cgggcgugcu ccugaaggag uucacgguga gcggcaacau ccugaccauc | 420 |
| cggcugaccg ccgcggacca ccggcagcug cagcugucga ucagcagcug ccuccagcag | 480 |
| cugagccugc ugauguggau cacccagugc uuccugccgg uguccuggc ccagccgccc | 540 |
| agcggccagc gccggugacc acuaguuaua agacugacua gcccgauggg ccucccaacg | 600 |
| ggcccuccuc cccuccuugc accgagauua auaaaaaaaa aaaaaaaaaa aaaaaaaaaa | 660 |
| aaaaaaaaaa aaaaaaaaaa aaaaaaaaaa aaaaaugca uccccccccc cccccccccc | 720 |
| cccccccccc ccaaaggcuc uuuucagagc caccagaauu | 760 |

<210> SEQ ID NO 4
<211> LENGTH: 1792
<212> TYPE: RNA
<213> ORGANISM: Artificial Sequence
<220> FEATURE:
<223> OTHER INFORMATION: GC-optimized Rabies virus glycoprotein mRNA

<400> SEQUENCE: 4

| | |
|---|---|
| gggagaaagc uuaccauggu gccccaggcc cugcucuucg uccgcugcu ggguguccc | 60 |
| cucugcuucg gcaaguuccc caucuacacc auccccgaca agcuggggcc guggagcccc | 120 |
| aucgacaucu ccaccugcuc cugccccaac aaccucgugg ucgaggacga gggcugcacc | 180 |
| aaccugagcg gguucuccua cauggagcug aagguggcu acaucagcgc caucaagaug | 240 |
| aacgggguuca cgugcaccgg cguggucacc gaggcggaga ccuacacgaa cuucgugggc | 300 |
| uacgugacca ccaccuucaa gcggaagcac uuccgcccca cgccggacgc cugccgggcc | 360 |
| gccuacaacu ggaagaugc cggggacccc cgcuacgagg aguccuccca caaccccuac | 420 |
| cccgacuacc acuggcugcg gaccgucaag accaccaagg agagccuggu gaucaucucc | 480 |
| ccgagcgugg cggaccucga ccccuacgac cgcuccccugc cagccgggu cuucccggc | 540 |
| gggaacugcu ccggcgugg cgugagcucc acguacugca gcaccaacca cgacuacacc | 600 |
| aucuggaugc ccgagaaccc gcgccugggg augccucugc acaucuucac caacagccgg | 660 |
| ggcaagcgcg ccuccaaggg cagcgagacg ugcgggguucg ucgacgagcg gggccucuac | 720 |
| aagucccuga ggggggccug caagcugaag cucugcggcg ugcugggccu cgcgcucaug | 780 |
| gacgggaccu ggguggcgau gcagaccagc aacgagacca aguggugccc cccggccag | 840 |
| cuggucaacc ugcacgacuu ccggagcgac gagaucgagc accucguggu ggaggagcug | 900 |
| gucaagaagc gcgaggagug ccuggacgcc cucgaguccca ucaugacgac caagagcgug | 960 |
| uccuuccggc gccugagcca ccugcggaag cucgugcccg gguucggcaa ggccuacacc | 1020 |
| aucuucaaca gacccugau ggaggccgac gcccacucaca aguccguccg cacguggaac | 1080 |
| gagaucaucc cgagcaaggg gugccugcgc gugggcggcc gcugccaccc ccacgucaac | 1140 |
| gggguguucu ucaacggcau cauccucggg cccgacggca cgugcugau ccccgagaug | 1200 |
| caguccagcc ugcuccagca gcacauggag cugcuggucu ccagcgugau cccgcucaug | 1260 |
| caccccccugg cggaccccuc caccguguuc aagaacgggg acgaggccga ggacuucguc | 1320 |
| gaggugcacc ugcccgacgu gcacgagcgg aucagcggcg ucgaccucgg ccugccgaac | 1380 |
| ugggggaagu acgugcugcu cuccgccggc gcccugaccg cccugaugcu gaucaucuuc | 1440 |
| cucaugaccu gcuggcgccg ggugaaccgg agcgagccca cgcagcacaa ccugcgcggg | 1500 |
| accggccggg agguucuccgu gaccccgcag agcggggaaga ucaucuccag cugggagucc | 1560 |

```
uacaagagcg gcggcgagac cgggcuguga ggacuaguua uaagacugac uagcccgaug    1620
ggccucccaa cgggcccucc ucccucccuu gcaccgagau uaauaaaaaa aaaaaaaaaa    1680
aaaaaaaaaa aaaaaaaaa aaaaaaaaa aaaaaaaaa aaaaaaaaug cauccccccc      1740
cccccccccc cccccccccc cccaaaggc ucuuucaga gccaccagaa uu              1792

<210> SEQ ID NO 5
<211> LENGTH: 1480
<212> TYPE: RNA
<213> ORGANISM: Artificial Sequence
<220> FEATURE:
<223> OTHER INFORMATION: GC-optimized human cancer antigen mRNA

<400> SEQUENCE: 5
gggagaaagc uuaccaugcc cggcggguge agccggggcc cggccgccgg ggacggccgc     60
cugcggcucg cgcgccuggc ccuggugcuc cuggggugg ucuccagcuc cagccccacc     120
uccagcgccu ccagcuucuc cagcuccgcc cccuuccugg ccagcgcggu guccgcccag    180
cccccgcucc ccgaccagug cccgccug ugcgagugca gcgaggccgc gcggaccgug      240
aagugcguca accgcaaccu gacggaggug cccaccgacc ucccggccua cgugcggaac    300
cuguuccuga ccggcaacca gcucgccguc cugcccgccg gcgccuucgc gcgccggccg    360
ccccuggccg agcucgccgc ccugaaccug uccgggagcc gccucgacga ggugcgggcc    420
ggcgcguucg agcaccugcc guccugcgc cagcucgacc ugagccacaa ccccuggcc     480 gaccucuccc ccuucgccuu cagcgggagc aacgccuccg ugagcgcccc cuccccgcug    540
gucgagcuga uccucaacca caucgugccc ccgaggacg agcggcagaa ccgcagcuuc     600
gagggcaugg uggucgcggc ccugcuggcc gggcgggccc uccagggccu gcgccggcug    660
gagcucgccu ccaaccacuu ccuguaccug ccccgcgacg ugcucgcgca gcugccgagc    720
cugcggcacc ucgaccuguc caacaacagc cuggugucc ucaccuacgu cagcuuccgc    780
aaccugacgc accuggaguc ccuccaccug gaggacaacg cccugaaggu gcugcacaac    840
ggcacccucg ccgagcugca ggggcugccc cacauccggg uguuccucga caacaacccc    900 uggggucugcg acugccacau ggccgacaug gugaccuggc ugaaggagac cgaggugguc    960
cagggcaagg accgccugac gugcgcguac cccgagaaga ugcggaaccg ggugcuccug    1020
gagcugaaca gcgccgaccu cgacugcgac ccgauccugc ccccucccu gcagaccagc    1080 uacguguucc ucgggaucgu ccuggcccug aucggcgcca ucuuccuccu ggugcuguac    1140
cucaaccgca agggcaucaa gaaguggaug cacaacaucc gggacgccug ccgcgaccac    1200
auggaggggu accacuaccg guacgagauc aacgcggacc ccgccugac caaccugucc    1260 agcaacuccg acgucugacc acuaguuaua agacugacua gcccgauggg ccucccaacg    1320 ggccccuccuc cccuccuugc accgagauua auaaaaaaaa aaaaaaaaaa aaaaaaaaa    1380 aaaaaaaaaa aaaaaaaaa aaaaaaaaa aaaaaugca ucccccccc ccccccccc        1440 cccccccccc ccaaaggcuc uuuucagagc caccagaauu                          1480
```

RNA ANALYSIS BY TOTAL HYDROLYSIS AND QUANTIFICATION OF RELEASED NUCLEOSIDES

This application is a national phase application under 35 U.S.C. § 371 of International Application No. PCT/EP2017/055048, filed Mar. 3, 2017, which claims benefit of International Application No. PCT/EP2016/054599, filed Mar. 3, 2016, the entire contents of each of which are hereby incorporated by reference.

FIELD OF THE INVENTION

The present invention relates to the field of RNA analysis. The invention provides a method suitable for use in quality control during or following production of RNA. The method is particularly useful for the determination of critical RNA quality attributes including RNA identity, RNA integrity, capping efficiency, poly(A) tail length, RNA oxidation, and the incorporation efficiency and amount of modified nucleotides.

BACKGROUND OF THE INVENTION

Ribonucleic acid (RNA) molecules represent an emerging class of drugs. RNA-based therapeutics may be used in immunotherapy, gene therapy and genetic vaccination, belonging to the most promising and quickly developing therapeutic fields of modern medicine. RNA-based therapeutics may provide highly specific and individual treatment options for therapy of a large variety of diseases.

For example, RNA-based therapeutics include mRNA molecules encoding antigens for use as vaccines (Fotin-Mleczek et al. (2012) J. Gene Med. 14(6):428-439). In addition, it is envisioned to use RNA molecules for replacement therapies, e.g. providing missing proteins such as growth factors or enzymes to patients. Furthermore, the therapeutic use of non-coding immunostimulatory RNA molecules and other non-coding RNAs such as microRNAs, siRNAs, CRISPR/Cas9 guide RNAs, and long non-coding RNAs is considered.

Short RNA molecules can be synthesized by chemical methods, whereas long RNAs are typically produced by in vitro transcription using suitable DNA templates with a promoter and RNA polymerases, for example bacteriophage SP6, T3 or T7 RNA polymerases which are able to bind to said promoter.

For the successful development of RNA-based therapeutics, the production of RNA molecules as active pharmaceutical ingredients must be efficient in terms of yield, quality, safety and costs, especially when RNA is produced at a large scale. Such quality controls may be implemented during RNA production and/or following RNA production and/or as a batch release quality control.

For any application of RNA in a scientific or therapeutic setting, it is highly desired or mandatory to use RNA with a defined sequence that can be reproduced in a reliable manner. Moreover, the 5' terminal as well as the 3' terminal region of a protein coding RNA molecule are known to be involved in the regulation of the mRNA stability and translation efficiency. The 5' cap structure and the 3' poly(A) tail are important features for the efficient translation of mRNA and protein synthesis in eukaryotic cells and, therefore, the produced RNA should be controlled for such key functional features.

Particularly, for therapeutic purposes, it is requested by the authorities to control the composition of the drug. Therefore, it is highly desired or mandatory to control the identity and/or integrity of the RNA molecules. Moreover, it is desired to control the produced RNA (in case of protein coding mRNA) for capping efficiency, and for the quality and length of the poly(A) tail or other homopolymeric sequence elements (e.g., poly(C) sequence). Furthermore, it could be shown that oxidation of RNA can lead to translational errors (Kumaya et al. (2006) Nucleic Acid Symposium Series 50: 99-100). Therefore it is desired to have a quality control to determine the oxidation status of the produced RNA. Additionally it is desirable to determine the incorporation efficiency and amount of modified nucleotides if used for RNA in vitro transcription.

For the quality control of chemically synthesized or in vitro transcribed RNA, several assays have been established in the art. For example, RNA identity can be analyzed using PCR based methods or sequencing. In addition, RNA integrity can be analyzed by electrophoretic methods. Moreover, several quality controls have been established in the art to analyze the capping efficiency (WO 2015/01416; Theus et al. (1990) Biotechniques Rapid Dispatches 9(5): 610-612) or to analyze poly(A) tails at the 3' end of an RNA (PCT/EP2015/001336).

Furthermore, HPLC-based methods have been described for determining the degree of RNA oxidation and the incorporation of modified nucleotides of cellular RNAs (Nees et al. (2014) Innate DNA and RNA Recognition, methods in Molecular Biology, vol. 1169: 3-14). The percentage of modified nucleosides can also be determined by separating the nucleosides by HPLC and subsequent quantification using GC/MS or LC/MS (Tanaka et al. (2012) Free Radical Biology and Medicine 53(4): 854-862; Su et al. (2014) Nature Protocols 9(4): 828-841).

Even though methods are described to analyze single features of the RNA, no method has been described which allows to analyze all of the above described different features of the RNA in one assay.

Therefore, no all-encompassing quality control has yet been described that allows to analyze the identity, the integrity, the capping degree, the length of a poly(A) tail, the length of other homopolymeric elements (e.g., a poly(C) sequence), the incorporation efficiency and amount of modified nucleotides, and the oxidation status of an RNA at the same time.

SUMMARY OF THE INVENTION

The present inventors have surprisingly found that total hydrolysis of RNA coupled with HPLC detection methods can be used as a quality control that addresses the above mentioned objective all in one assay. The described inventive method wherein hydrolysates of RNA species are analysed using HPLC is a particularly powerful quality control for chemically synthesized and in vitro transcribed RNA. Using the HPLC analysis, critical quality parameters such as RNA identity, RNA integrity, RNA capping efficiency, RNA polyadenylation, RNA oxidation and the incorporation ratio of modified nucleotides can be determined in one method.

An RNA species, comprising a poly(A) tail and a cap-structure, produced via RNA in vitro transcription, was hydrolyzed to individual nucleoside monophosphates. After dephosphorylation, the nucleosides A, C, m7G (cap analogue), G, U and 8-OH-GTP (oxidized GTP) were separated and quantified by HPLC.

By quantifying the nucleosides U, G and C, the inventors determined the identity and the molarity of the RNA (comprising a poly(A) tail). In addition, the quantification of the m7G cap analogue allowed for a calculation of the capping degree of the RNA.

With the amount of A nucleosides, the length of the poly(A) tail was determined. Optionally, the quality of other homopolymeric elements such as a poly(C) sequence can be determined. With the amount of modified nucleotides, the frequency of incorporation and the amount of modified nucleotides was calculated. Moreover, the oxidation status of the RNA was determined by detecting and quantifying oxidized nucleosides.

Hence, the present invention relates to a method for analyzing a sample comprising RNA molecules transcribed from a template DNA with known sequence and length or chemically synthesized with known sequence and length, comprising the steps of:

a) providing a sample comprising RNA molecules;
b) completely hydrolyzing the RNA molecules, thereby releasing nucleosides;
c) separating and quantifying the released nucleosides by HPLC;
d) determining at least one of:
  the number of copies of the RNA molecules in the sample,
  the matching of the sequence of the RNA molecules with that of the known sequence,
  the matching of the length of the RNA molecules with the known length,
  the capping degree of the RNA molecules within the sample, and
  the length of homopolymeric elements in the RNA molecules.

Step d) may further comprise determining at least one of:
the incorporation and amount of modified nucleotides into the RNA molecules, and
the oxidation status of the RNA molecules.

Step d) may also comprise determining:
the number of copies of the RNA molecules in the sample,
the matching of the sequence of the RNA molecules with that of the known sequence,
the matching of the length of the RNA molecules with the known length,
the capping degree of the RNA molecules within the sample,
the length of homopolymeric elements in the RNA molecules,
the incorporation and amount of modified nucleotides into the RNA molecules, and
the oxidation status of the RNA molecules.

The RNA molecules may be provided by chemical synthesis or by in vitro transcription.

The method may further comprise a step a1) of purifying the RNA molecules, preferably by HPLC.

The RNA molecules may be completely hydrolyzed by enzyme treatment, preferably by treatment with a nuclease, a phosphatase and a phosphodiesterase.

More preferably, the nuclease is Nuclease P1 from *Penicillium citrinum*, the phosphodiesterase is Phosphodiesterase I from *Crotalus adamanteus* and/or the phosphatase is shrimp alkaline phosphatase.

In step c) the nucleosides may be separated using an octadecyl capped silica column.

In one embodiment, a mobile phase comprising an aqueous solvent is used in the HPLC of step c). Preferably, the aqueous solvent is ammonium acetate and more preferably, the aqueous solvent is 5 mM $NH_4OAc$, pH 6.

In the HPLC of step c) the nucleosides may be eluted with an organic solvent, preferably with a linear gradient of said organic solvent. More preferably, the gradient is from 0% to 20% of the organic solvent. In one embodiment, the organic solvent is 40% v/v acetonitrile.

Step c) may further comprise detecting the released nucleosides and identifying the released nucleosides by comparison to a standard for each nucleoside.

Preferably, the released nucleosides are quantified by determining the peak area for each of the nucleosides and comparing it to a standard curve.

In one embodiment, the RNA molecules are polyadenylated and step d) comprises determining the number of copies of the RNA (n(RNA)) molecules in the sample by using formula 1.1:

$$n(RNA)=\frac{1}{3}*(n(C)/u(C)+n(G)/u(G)+n(U)/u(U)),$$

wherein n(C), n(U), and n(G) is the measured content of the corresponding nucleoside and any modifications thereof in the sample, and u(C), u(U), and u(G) is the number of the corresponding nucleoside and any modifications thereof in the expected sequence of the RNA molecules.

In another embodiment, the RNA molecules are not polyadenylated and step d) comprises determining the number of copies of the RNA (n(RNA)) molecule in the sample by using formula 1.2:

$$n(RNA)=\frac{1}{4}*(n(C)/u(C)+n(G)/u(G)+n(U)/u(U)+n(A)/u(A)),$$

wherein n(C), n(U), n(G) and n(A) is the measured content of the corresponding nucleoside and any modifications thereof in the sample, and n(C), n(U), n(G) and n(A) is the number of the corresponding nucleoside and any modifications thereof in the expected sequence of the RNA molecules.

Step d) may comprise determining the matching of the sequence of the RNA molecules with the known sequence and/or the matching of the length of the RNA molecules with the known length by comparing the measured ratio of a specific nucleoside in the sample with the expected ratio of said nucleoside.

In one embodiment, the RNA molecules are polyadenylated and the measured ratio of a specific nucleoside in the sample is determined using formula 2.1:

$$rm(X)=n(X)/[n(C)+n(G)+n(U)]$$

and the expected ratio of said nucleoside is determined using formula 3.1:

$$re(X)=u(X)/[u(C)+u(G)+u(U)],$$

wherein rm is the measured ratio of a specific nucleoside in the sample, re is the expected ratio of the corresponding nucleoside in the RNA molecules, n(C), n(U), and n(G) is the measured content of the corresponding nucleoside and any modifications thereof in the sample, u(C), u(U), and u(G) is the number of the corresponding nucleoside and any modifications thereof in the expected sequence of the RNA molecules, and X is a nucleotide selected from C, G and U and is the same nucleotide for both rm(X) and re(X).

In another embodiment, the RNA molecules are not polyadenylated and the measured ratio of a specific nucleoside in the sample is determined using formula 2.2:

$$rm(X)=n(X)/[n(C)+n(G)+n(U)+n(A)]$$

and the expected ratio of said nucleoside is determined using formula 3.2:

$$re(X)=u(X)/[u(C)+u(G)+u(U)+n(A)],$$

wherein rm is the measured ratio of a specific nucleoside in the sample, re is the expected ratio of the corresponding nucleoside in the RNA molecules, n(C), n(U), n(G) and n(A) is the measured content of the corresponding nucleoside and any modifications thereof in the sample, n(C), n(U), n(G) and n(A) is the number of the corresponding nucleoside and any modifications thereof in the expected sequence of the RNA molecules, and X is a nucleotide selected from C, G, U or A.

The measured and the expected ratio may be determined for each of C, G, U and/or A.

In one embodiment, a mismatch between the values for rm and re indicates no matching of the sequence of the RNA molecules with the known sequence and/or no matching of the length of the RNA molecules with the known length.

Step d) may comprise determining the capping degree of the RNA molecules within the sample by using formula 4:

$$cap=n(CA)/n(RNA)*100\%,$$

wherein % cap is the percentage of capped RNA molecules, n(CA) is the content of a cap analogue in the sample, and n(RNA) is the number of copies of the RNA molecules in the sample.

The cap analogue may be selected from the group consisting of: G[5]ppp[5]G, m7G[5']ppp[5]G, m32,2,7G[5]ppp[5]G, m27,3'-OG[5]ppp[5]G (3'-ARCA), m27,2'-OGpppG (2'-ARCA), m27,2'-OGppspG D1 (β-S-ARCA D1) and m27,2'-OGppspG D2 (β-S-ARCA D2).

The number of copies of the RNA molecules in the sample may be determined as described above for polyadenylated and not polyadenylated RNA molecules.

Step d) may comprise determining the length of a homopolymeric element in the RNA molecules by using formula 5:

$$l_x m = n(X)/n(RNA) - [u(X) - l_x e],$$

wherein $l_x m$ is the calculated average length of the poly(X) stretch, n(X) is the measured content of a nucleoside X forming the homopolymeric element in the sample, n(RNA) is the number of copies of the RNA molecules in the sample, u(X) is the number of X in the expected sequence of the RNA molecules, $l_x e$ is the expected average length of the poly(X) stretch in the RNA molecules.

In one embodiment, the homopolymeric element is a poly(A) stretch and wherein the length of the poly (A) stretch is determined by using formula 5.1:

$$l_A m = n(A)/n(RNA) - [u(A) - l_A e];$$

wherein $l_A m$ is the calculated average length of the poly(A) stretch, n(A) is the measured content of the nucleoside A in the sample, n(RNA) is the number of copies of the RNA molecules in the sample, u(A) is the number of nucleoside A in the expected sequence of the RNA molecules, and $l_A e$ is the expected average length of the poly(A) stretch in the RNA molecules.

The number of copies of the RNA molecules in the sample may be determined as described above.

Step d) may comprise determining the incorporation of modified nucleosides into the RNA molecules by using formula 6:

$$\% mN = n(mN)/[n(uN)+n(mN)]*100\%,$$

wherein % mN is the percent incorporation of a modified nucleoside in the RNA molecules, n(mN) is the measured content of the modified nucleoside in the RNA molecules, and n(uN) is the measured content of the unmodified nucleoside in the RNA molecules.

The modified nucleoside may be selected from the group consisting of: 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

The modified nucleosides may be oxidized nucleosides and % mN may indicate the oxidation status of the RNA molecules.

The oxidized nucleosides may be selected from the group consisting of: 8-hydroxyguanosine (8-OHG), 8-oxo-7,8-dihydro-2'-deoxyguanosine, dehydroguanidinohyantoin, 2,4,6-trioxo-[1,3,5]triazinane-1-carboxamidine, N-nitro-dehydroguanidinohydantoin, spiroiminodihydantoin, guanidinohydantoin, 4-hydroxy-2,5-dioxo-imidazolidine-4-carboxylic acid, 3-nitrotyrosine, 3.3'-dityrosine, 3-hydroxy-5-imino-3,3a,4,5-tetrahydro-1H-imidazo[4,5-d]imidazol-2-one, parabanic acid, cyanuric acid, 4-hydroxy-8-oxo-4,8-dihydro-2'-desoxyguanosine, 4,5-dihydro-5-hydroxy-4-(nitrosooxy)-2-desoxyguanosine, 2-amino-5 [(2-deoxy-β-D-erythro-pentofuranpsyl)amino]-4H-imidazol-4-one, 2,2-diamino-4-[(2-deoxy-β-D-erythro-pentofuranpsyl)amino]-5-(2H)-oxazolone, 5-[hydroxymethyl]-uracil, 2-thiobarbituric acid, 8-nitroguanine, hypoxanthine, uracil, thymine and xanthine.

Preferably, the RNA molecules are mRNA molecules.

The method may additionally comprise step a1) of modifying the RNA molecules.

The modifying of the RNA molecules may comprise enzymatically adding a poly(A) stretch to the RNA molecules.

In this case, step d) may comprise determining the length of the enzymatically added poly(A) stretch of the RNA molecules by using formula 5.1:

$$l_A m = n(A)/n(RNA) - [u(A) - l_A e],$$

wherein $l_A m$ is the calculated average length of the poly(A) stretch, $n(A)$ is the measured content of nucleoside A in the sample, $n(RNA)$ is the number of copies of the RNA molecules in the sample, $u(A)$ is the number of nucleoside A in the expected sequence of the RNA molecules, and $l_A e$ is the expected average length of the poly(A) stretch in the RNA molecules.

The number of copies of the RNA molecules in the sample may be determined as described above.

The modifying of the RNA molecules may also comprise enzymatically adding a cap structure to the RNA molecules.

In this case, the capping degree of the RNA molecules within the sample is determined by using formula 4:

$$\% \text{ cap} = n(CA)/n(RNA) * 100\%,$$

wherein % cap is the percentage of the capped RNA molecules, n(CA) is the content of a cap analogue in the sample, and n(RNA) is the number of copies of the RNA molecules in the sample.

The number of copies of the RNA molecules in the sample may be determined as described above.

The modifying of the RNA molecules may also comprise enzymatically modifying the nucleotides of the RNA molecules.

In this case, the percentage of enzymatically modified nucleosides in the RNA molecules is determined by using formula 6:

$$\% \ mN = n(mN)/[n(uN) + n(mN)] * 100\%,$$

wherein % mN is the percentage of a modified nucleoside in the RNA molecules, n(mN) is the measured content of the modified nucleoside in the RNA molecules, and n(uN) is the measured content of the unmodified nucleoside in the RNA molecules.

The present invention also relates to the use of the method according to the invention in the quality control of RNA prepared by RNA in vitro transcription or by chemical synthesis.

DEFINITIONS

Figure 1:
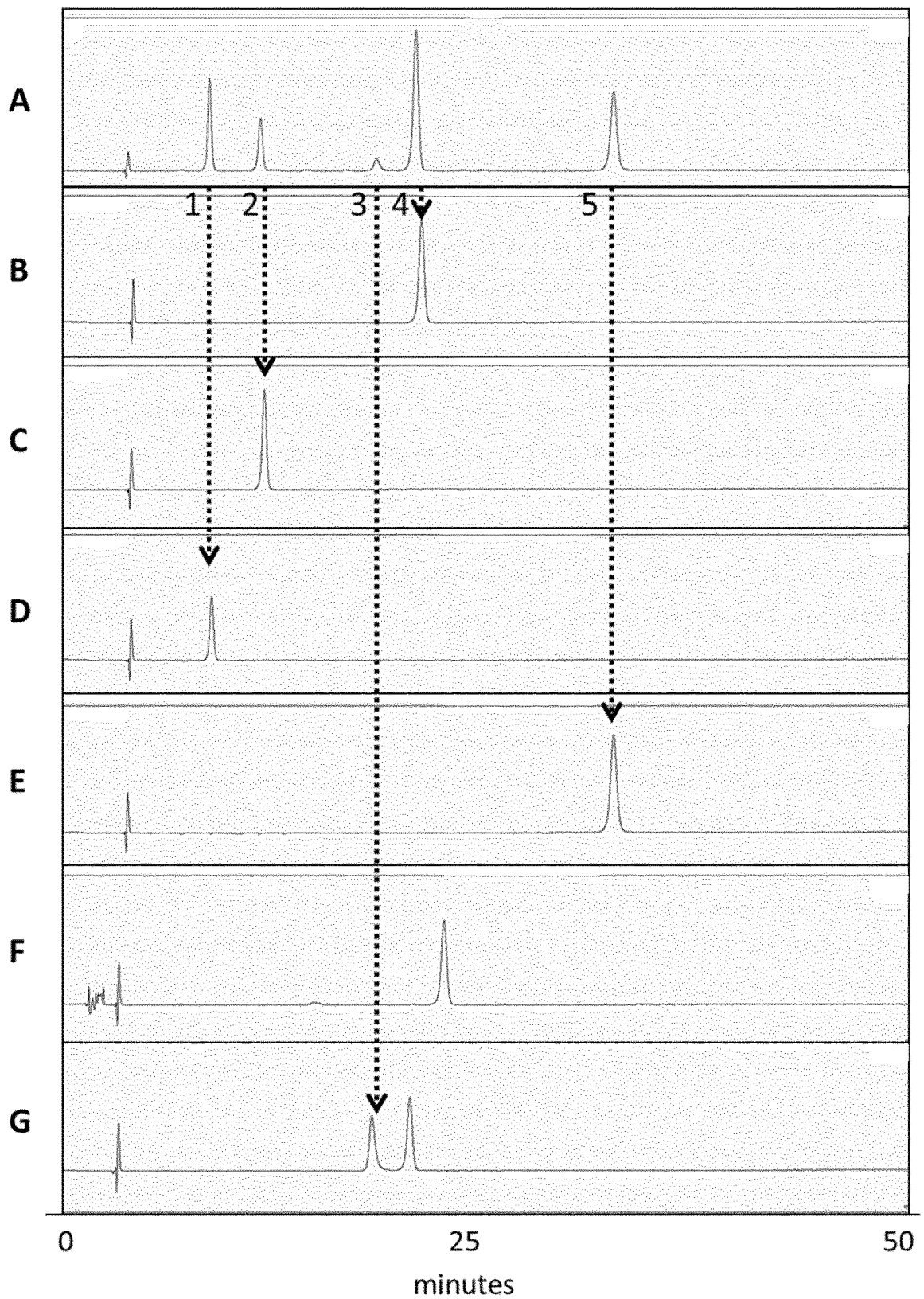
FIG. 1: shows an exemplary chromatogram of the hydrolysate of PpLuc mRNA (R2988) and respective chromatograms of standards for calibration. The following chromatograms are shown (from top to bottom): PpLuc hydrolysate (A), GTP standard (B), UTP standard (C), CTP standard (D), ATP standard (E), 8-OH-GTP standard (F) and m7GpppG cap analogue standard (G). The arrows show how corresponding peaks in the hydrolysate were identified using the standards. For experimental details see Example 3.

For the sake of clarity and readability the following definitions are provided. Any technical feature mentioned in these definitions may be read on each and every embodiment of the invention. Additional definitions and explanations may be specifically provided in the context of these embodiments.

RNA, mRNA: RNA is the usual abbreviation for ribonucleic acid. It is a nucleic acid molecule, i.e. a polymer consisting of nucleotide monomers. These nucleotides are usually adenosine monophosphate (AMP), uridine monophosphate (UMP), guanosine monophosphate (GMP) and cytidine monophosphate (CMP) monomers or analogues thereof, which are connected to each other along a so-called backbone. The backbone is formed by phosphodiester bonds between the sugar, i.e. ribose, of a first and a phosphate moiety of a second, adjacent monomer. The specific order of the monomers, i.e. the order of the bases linked to the sugar/phosphate-backbone, is called the RNA sequence. Usually RNA may be obtainable by transcription of a DNA sequence, e.g., inside a cell. In eukaryotic cells, transcription is typically performed inside the nucleus or the mitochondria. In vivo, transcription of DNA usually results in the so-called premature RNA (also called pre-mRNA, precursor mRNA or heterogeneous nuclear RNA) which has to be processed into so-called messenger RNA, usually abbreviated as mRNA. Processing of the premature RNA, e.g. in eukaryotic organisms, comprises a variety of different post-transcriptional modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein.

Typically, a mature mRNA comprises a 5'-cap, optionally a 5'UTR, an open reading frame, optionally a 3'UTR and a poly(A) tail.

In addition to messenger RNA, several non-coding types of RNA exist which may be involved in regulation of transcription and/or translation, and immunostimulation. Within the present invention the term "RNA" further encompasses any type of single stranded (ssRNA) or double stranded RNA (dsRNA) molecule known in the art, such as viral RNA, retroviral RNA and replicon RNA, small interfering RNA (siRNA), antisense RNA (asRNA), circular RNA (circRNA), CRISPR/Cas9 guide RNA, ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA).

Sample comprising RNA molecules: The term "sample comprising RNA molecules" is intended to include a sample comprising a population of RNA molecules which have been transcribed from the same template DNA of known sequence. A sample comprising RNA molecules will therefore comprise many RNA molecules of the same sequence, although any modifications including polyadenylation, capping, incorporation of modified nucleotides may not occur at the same rate on all of them so that the final structure of the RNA molecules within the sample may not be the same for all the RNA molecules. The sample comprising RNA molecules does not comprise RNA molecules which have been transcribed from two or more different DNA templates.

Expected sequence: The term "expected sequence" refers to the sequence identical to the known sequence of the template used for RNA in vitro transcription or the sequence used for chemical synthesis, i.e. the desired sequence.

Expected length: The term "expected length" refers to the length of the RNA molecule which could be expected from the known length of the template used for RNA in vitro transcription or the sequence used for chemical synthesis, i.e. the desired length.

Hydrolysis/hydrolyzing: RNA hydrolysis is a reaction in which a phosphodiester bond in the sugar-phosphate backbone of RNA is broken, thereby cleaving the RNA molecule into shorter stretches. RNA is susceptible to hydrolysis because the ribose sugar in RNA has a hydroxyl group at the 2' position. This feature makes RNA chemically unstable compared to DNA, which does not have this 2' OH group and thus is not susceptible to base-catalyzed hydrolysis. RNA hydrolysis occurs when the deprotonated 2' OH of the ribose, acting as a nucleophile, attacks the adjacent phosphorus in the phosphodiester bond of the sugar-phosphate backbone of the RNA, resulting in a transition state in which the phosphorus is bonded to five oxygen atoms. The phosphorus then detaches from the oxygen connecting it to the adjacent sugar, resulting in ester cleavage of the RNA backbone. This produces a 2',3'-cyclic phosphate that can then yield either a 2'- or a 3'-nucleotide when hydrolyzed. This hydrolysis can occur spontaneously, then called autohydrolysis. RNA hydrolysis is increased if the pH of the RNA solution is alkaline (alkaline hydrolysis).

Alternatively, the RNA may be hydrolyzed enzymatically by the action of phosphodiesterases, which are capable of breaking the phosphodiester bonds that make up the backbone of the RNA molecule.

Complete hydrolysis: Complete hydrolysis is achieved when the RNA molecule has been hydrolyzed to an extent that no phosphodiester bridges remain between nucleotides, i.e. the backbone of the RNA molecule has been completely disassembled into single nucleotides. Hence, no longer nucleotide stretches comprising two or more nucleotides linked by phosphodiester bridges can be detected. Hydrolysis of an RNA molecule can be achieved by enzymatic hydrolysis (e.g., using nucleases, phosphodiesterases) or e.g. by alkaline hydrolysis, for example by incubating an RNA sample in alkaline hydrolysis buffer (e.g., 50 mM sodium carbonate [$NaHCO_3$/$Na_2CO_3$] pH 9.2, 1 mM EDTA) at 95° C. until complete hydrolysis has occurred. For the purpose of this invention, complete hydrolysis also includes treatment with a phosphatase that dephosphorylates the released, single nucleotides into single nucleosides.

Phosphodiesterase: A phosphodiesterase (PDE) is any enzyme that breaks a phosphodiester bond. Phosphodiesterase families include cyclic nucleotide phosphodiesterases, phospholipases C and D, autotaxin, sphingomyelin phosphodiesterase, DNases, RNases, and restriction endonucleases, as well as numerous less-well-characterized small-molecule phosphodiesterases. Of these, several can catalyze cleavage at specific sites on an RNA molecule by breaking the phosphodiester backbone of the molecule, for example nucleases and ribonucleolytic ribozymes.

Suitable phosphodiesterases for use in the present invention include phosphodiesterase I from *Crotalus* adamanteus, phosphodiesterase I from *Bothrops atrox*, phosphodiesterase I from *Crotalus atrox* and phosphodiesterase from bovine spleen. A preferred phosphodiesterase for use in the present invention is phosphodiesterase I from *Crotalus adamanteus* (available from Sigma Aldrich).

Nuclease: A nuclease is a phosphodiesterase capable of cleaving the phosphodiester bonds between the nucleotide subunits of nucleic acids. Nucleases are usually further divided into endonucleases, which cleave phosphodiester bonds within a nucleotide chain, and exonucleases, which cleave phosphodiester bonds at either terminus of the nucleic acid, although some of the enzymes may fall in both categories. Well known nucleases are deoxyribonuclease and ribonuclease.

Suitable nucleases for use in the present invention include benzonase, nuclease P1 from *Penicillium citrinum*, nuclease S1 from *Aspergillus oryzae*, ribonuclease A from bovine pancreas and ribonuclease T1 from *Aspergillus oryzae*. A preferred nuclease for use in the present invention is nuclease P1 from *Penicillium citrinum* (available from Sigma Aldrich).

Exoribonucleases: Exoribonucleases degrade RNA from the 5' or 3' end of the RNA molecule. These enzymes are involved in the degradation of many different RNA species, including mRNA, tRNA, rRNA and miRNA. Exoribonucleases can be single proteins (such as Nuclease P1 from *Penicillium citrinum* and PDE1 from *Crotalus adamanteus*, 5'→3' and 3'→5' exoribonucleases, respectively) or complexes of multiple proteins, such as the exosome complex, in which four of the major exoribonuclease families are represented.

Phosphatase: A phosphatase is an enzyme that removes a phosphate group from its substrate by hydrolyzing phosphoric acid monoesters into a phosphate ion and a molecule with a free hydroxyl group. Examples include alkaline phosphatase, deoxyribonucleotide phosphatases, ribonucleotide phosphatases, pyrophosphatases, and protein phosphatases, which remove a phosphate group from the phosphorylated amino acid residue of the substrate protein. In the present invention, the phosphatase is preferably an alkaline phosphatase, such as shrimp alkaline phosphatase, calf-intestinal alkaline phosphatase, placental alkaline phosphatase, and its C terminally truncated version secreted alkaline phosphatase. Most preferred is shrimp alkaline phosphatase (available from New England Biolabs).

HPLC: HPLC is the common abbreviation of the term "high performance liquid chromatography". In the HPLC process a pressurized liquid solvent containing the sample mixture is passed through a column filled with a solid adsorbent material leading to the interaction of components of the sample with the adsorbent material. Since different components interact differently with the adsorbent material, this leads to the separation of the components as they flow out of the column. The operational pressure in HPLC process is typically between 50 and 350 bar. The term HPLC includes reversed phase HPLC (RP-HPLC), size exclusion chromatography, gel filtration, affinity chromatography, hydrophobic interaction chromatography or ion pair chromatography, wherein reversed phase HPLC is preferred.

Reversed phase HPLC: Reversed phase HPLC uses a non-polar stationary phase and a moderately polar mobile phase and therefore is based on hydrophobic interactions which result from repulsive forces between a relatively polar solvent, the relatively non-polar analyte, and the non-polar stationary phase (reversed phase principle). The retention time on the column is therefore longer for molecules which are more non-polar in nature, allowing polar molecules to elute more readily. The retention time is increased by the addition of polar solvent to the mobile phase and decreased by the addition of more hydrophobic solvent.

The characteristics of the specific RNA molecule as an analyte may play an important role in its retention characteristics. In general, an analyte having more apolar functional groups results in a longer retention time because it increases the molecule's hydrophobicity and therefore the interaction with the non-polar stationary phase. Very large molecules, however, can result in incomplete interaction between the large analyte surface and the alkyl chain. Retention time increases with hydrophobic surface area which is roughly inversely proportional to solute size. Branched chain compounds elute more rapidly than their corresponding isomers because the overall surface area is decreased.

Separation/separating: The term "separating/separation" of nucleosides refers to the separation of all different nucleosides U, C, G and possibly A present in a nucleic acid molecule from each other based on their differential interactions with the adsorbent material due to their various characteristics such as, for example, size, charge, branching, or apolar or polar functional groups. The more a nucleoside interacts with the adsorbent material, the longer it is retained, i.e. the longer is its retention time. Based on their retention time, nucleosides will therefore elute at different times, and can be segregated into separate, distinct fractions that will only contain one type of nucleoside. Thereby, each of the separated nucleosides can be identified and quantified accurately.

Content of RNA molecules: The content of RNA molecules in a sample is the number of copies of said molecules present in the sample.

Identity of RNA molecules: During quality control of RNA production it is crucial to demonstrate that the sequence of the produced RNA molecules corresponds to or matches with the desired or expected or known sequence of the RNA molecule, i.e. that the RNA in vitro transcription or chemical synthesis of the RNA worked and did not produce any errors. This sequence identity of the RNA molecules can either be assessed according to the method disclosed herein or by e.g. sequencing.

Integrity of RNA molecules: The term "integrity" describes whether the complete RNA molecule is obtained and maintained. Accordingly, the integrity can be determined by measuring the length of the RNA molecule. If the complete RNA molecule is obtained, the RNA molecule obtained will have the expected or known length. If an incomplete RNA molecule is obtained, the length of the RNA molecule will be different from the expected or known length. Low integrity or differences in the length of the RNA molecule could be due to, amongst others, degradation, cleavage, incorrect basepairing, lack of or incomplete capping, lack of or incomplete polyadenylation, or incomplete transcription. This will become evident in a mismatch between measured and known, expected nucleoside ratios for the RNA molecules. However, such a mismatch could also be due to low identity, and additional sequence analysis is required to differentiate between low integrity and low identity, i.e. RNA molecules having a different length as the expected length, but the same sequence as the expected or known sequence, and RNA molecules having the same length as the expected or known length, but a sequence different from the expected sequence.

Cap structure: A 5' cap is typically a modified nucleotide, particularly a guanine nucleotide, added to the 5' end of an RNA molecule. Preferably, the 5' cap is added using a 5'-5'-triphosphate linkage. A 5' cap may be methylated, e.g. m7GpppN, wherein N is the terminal 5' nucleotide of the nucleic acid carrying the 5' cap, typically the 5'-end of an RNA. The naturally occurring 5' cap is m7GpppN (cap 0).

Further examples of 5'cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety.

Additionally, 5' cap structures can be further methylated, e.g. cap 1 (methylation of the ribose of the adjacent nucleotide of m7G), cap 2 (methylation of the ribose of the $1^{st}$ and $2^{nd}$ nucleotide downstream of the m7G), cap 3 (methylation of the ribose of the $1^{st}$ and $2^{nd}$ and $3^{rd}$ nucleotide downstream of the m7G) and cap 4 (methylation of the ribose of the $1^{st}$, $2^{nd}$, $3^{rd}$ and $4^{th}$ nucleotide downstream of the m7G).

A 5' cap structure may be formed by a cap analogue.

A 5' cap structure may be formed in chemical RNA synthesis or RNA in vitro transcription (co-transcriptional capping) or a cap structure may be formed in vitro using capping enzymes (e.g., commercially available capping kits).

Cap analogue: A cap analogue refers to a non-polymerizable di-nucleotide that has cap functionality in that it facilitates translation or localization, and/or prevents degradation of the RNA molecule when incorporated at the 5' end of the RNA molecule. Non-polymerizable means that the cap analogue will be incorporated only at the 5'terminus because it does not have a 5' triphosphate and therefore cannot be extended in the 3' direction by a template-dependent RNA polymerase.

Cap analogues include, but are not limited to, a chemical structure selected from the group consisting of m7GpppG, m7GpppA, m7GpppC; unmethylated cap analogues (e.g., GpppG); dimethylated cap analogue (e.g., m2,7GpppG), trimethylated cap analogue (e.g., m2,2,7GpppG), dimethylated symmetrical cap analogues (e.g., m7Gpppm7G), or anti reverse cap analogues (e.g., ARCA; m7,2'OmeGpppG, m7,2'dGpppG, m7,3'OmeGpppG, m7,3'dGpppG and their tetraphosphate derivatives) (Stepinski et al., 2001. RNA 7(10):1486-95). Examples of cap analogues are shown in Table 1.

Further cap analogues have been described previously (U.S. Pat. No. 7,074,596, WO 2008/016473, WO 2008/157688, WO 2009/149253, WO 2011/015347, and WO 2013/059475). The synthesis of $N^7$-(4-chlorophenoxyethyl) substituted dinucleotide cap analogues has been described recently (Kore et al. (2013) Bioorg. Med. Chem. 21(15): 4570-4).

TABLE 1

Cap analogues (D1 and D2 denote counterpart diastereoisomers)

| Triphosphate cap analogue | Tetraphosphate cap analogue |
|---|---|
| $m^7Gp_3G$ | $m^7Gp_4G$ |
| $m_2^{7,3'-O}Gp_3G$ | $b^7Gp_4G$ |
| $b^7Gp_3G$ | $b^7m^{3'-O}Gp_4G$ |
| $e^7Gp_3G$ | $m_2^{2,7}Gp_4G$ |
| $m_2^{2,7}Gp_3G$ | $m_3^{2,2,7}Gp_4G$ |
| $m_3^{2,2,7}Gp_3G$ | $b^7m^2Gp_4G$ |
| $m^7Gp_32'dG$ | $m7Gp^4m^7G$ |
| $m^7Gp_3m^{2'-O}G$ | |
| $m^7Gp_3m^7G$ | |
| $m_2^{7,2'-O}Gp_3G$ | |
| $m_2^{7,2'-O}GpppsG$ (D1) | |
| $m_2^{7,2'-O}GpppsG$ (D2) | |
| $m_2^{7,2'-O}GppspG$ (D1) | |
| $m_2^{7,2'-O}GppspG$ (D2) | |
| $m_2^{7,2'-O}GpsppG$ (D1) | |
| $m_2^{7,2'-O}GpsppG$ (D2) | |

Particularly preferred cap analogues are G[5']ppp[5']G, $m^7G[5']ppp[5']G$, $m3^{2,2,7}G[5']ppp[5']G$, $m2^{7,3'-O}G[5']ppp[5']G$ (3'-ARCA), $m2^{7,2'-O}$ GpppG (2'-ARCA), $m2^{7,2'-O}$ GppspG D1 (β-S-ARCA D1) and $m_2^{7,2'-O}GppspG$ D2 (β-S-ARCA D2).

Capping degree: The relative amount (in percent) of capped RNA molecules with respect to the total amount of RNA molecules in the sample is also referred to herein as "capping degree".

In one embodiment, the relative amount (in percent) of capped and non-capped RNA molecules to be analyzed is calculated using the following formulas 4.1 and 4.2:

$$\text{capped } RNA \text{ } (\%) = \frac{\text{amount of capped } RNA}{\Sigma \text{ amount (non-capped } RNA + \text{capped } RNA)} \times 100$$

$$\text{non-capped } RNA \text{ } (\%) = \frac{\text{amount non-capped } RNA}{\Sigma \text{ amount (non-capped } RNA + \text{capped } RNA)} \times 100$$

wherein Σ amount (non-capped RNA+capped RNA) refers to the total amount of RNA in the sample.

Homopolymeric element: Homopolymeric elements are stretches (sequences) in an RNA molecule consisting entirely or almost entirely of a single, repeated nucleotide. The most prominent homopolymeric element in RNA is the poly(A) tail at the 3' end of eukaryotic mRNA. In eukaryotes, polyadenylation, or addition of a poly(A) tail to an mRNA, is part of the process that produces mature mRNA for translation. It therefore forms part of the process of gene expression. The process of polyadenylation begins as the transcription of a gene terminates. The 3'-most segment of the newly made pre-mRNA is first cleaved off by a set of proteins; these proteins then synthesize the poly(A) tail at the RNA's 3' end. In some genes, these proteins may add a poly(A) tail at any one of several possible sites. Therefore, polyadenylation can produce more than one molecule from a single transcript (alternative polyadenylation), similar to alternative splicing.

The poly(A) tail is important for the nuclear export, translation, and stability of mRNA. The tail is shortened over time, and, when it is short enough, the mRNA is enzymatically degraded. However, in a few cell types, mRNAs with short poly(A) tails are stored for later activation by re-polyadenylation in the cytosol. In contrast, when polyadenylation occurs in bacteria, it promotes RNA degradation. This is also sometimes the case for eukaryotic non-coding RNAs. mRNA molecules in both prokaryotes and eukaryotes have polyadenylated 3'-ends, with the prokaryotic poly(A) tails generally being shorter and present on fewer mRNA molecules.

For the production of polyadenylated RNA, in vitro polyadenylation kits are available that use poly(A) polymerase, which uses ATP as a substrate for template-independent addition of adenosine monophosphates to the 3'-hydroxyl terminus of RNA molecules. They typically produce a poly(A)-tail length of ~150 bases, but can be adapted to adjust the length of the poly(A)-tails generated. Alternatively, poly(A) tails can be produced during RNA in vitro transcription, if the DNA template used for in vitro transcription encodes a poly(A) tail or a poly(A) tail can be generated by chemical synthesis.

Another homopolymeric element of note is a poly(C) stretch, or C-rich stability element. A poly(C) sequence is understood to be a sequence of cytosine residues, e.g., of up to about 400 nucleotides, e.g. from about 20 to about 400, preferably from about 50 to about 400, more preferably from about 50 to about 300, even more preferably from about 50 to about 250, most preferably from about 60 to about 250 nucleotides, which is preferably added to the 3'-terminus of an RNA, in particular mRNA. A poly(C) sequence is typically located at the 3'-end of an (m)RNA, but 5' of any poly(A) tail.

Differences in the stability of individual mRNAs can dramatically affect the overall level of gene expression. Eukaryotic mRNAs can have half-lives that vary from as short as several minutes to as long as several days. In differentiating human erythroid cells the deposition of high levels of alpha globin protein is dependent on an unusually long half-life of the alpha globin mRNA (greater than 24 hrs). The stability determinant for alpha globin mRNA has been mapped to a pyrimidine-rich segment of its 3' UTR. This poly(C) stretch confers stability by directing the assembly of a specific alpha ribonucleoprotein complex at this site. Other highly stable eukaryotic mRNAs that assemble the alpha globin protein complex at homologous pyrimidine-rich regions within their 3'UTRs are rabbit lipoxygenase, rat tyrosine hydroxylase, and human alpha(I)-collagen.

Other homopolymeric elements include poly(U) stretches that are known from viral RNA (e.g., coronavirus).

Modified nucleoside: The term "modified nucleoside" as used herein refers to chemical modifications comprising backbone modifications as well as sugar modifications or base modifications. These modified nucleosides are herein also called (nucleotide) analogues.

In this context, the modified nucleosides as defined herein are nucleotide analogues/modifications, e.g. backbone modifications, sugar modifications or base modifications. A backbone modification in connection with the present invention is a modification in which phosphates of the backbone of the nucleotides are chemically modified. A sugar modification in connection with the present invention is a chemical modification of the sugar of the nucleotides. Furthermore, a base modification in connection with the present invention is a chemical modification of the base moiety of the nucleotides. In this context nucleotide analogues or modifications are preferably selected from nucleotide analogues which are applicable for transcription and/or translation.

Sugar Modifications

The modified nucleosides and nucleotides which may be used in the context of the present invention can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), —O(CH$_2$CH$_2$O)nCH$_2$CH$_2$OR; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. NH$_2$; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified nucleotide can include nucleotides containing, for instance, arabinose as the sugar.

Backbone Modifications

The phosphate backbone may further be modified in the modified nucleosides and nucleotides. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications

The modified nucleosides and nucleotides, which may be used in the present invention, can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In some embodiments, the nucleotide analogues/modifications are selected from base modifications, which are preferably selected from 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl inosine-5'-triphosphate 4-thiouridine-5'-triphosphate, 5-aminoallylcytidine-5'-triphosphate, 5-amino allyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudo iso cytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleoside can be modified on the major groove face and can include replacing hydrogen on C-5 of uracil with a methyl group or a halo group.

In specific embodiments, a modified nucleoside is 5'-O-(1-Thiophosphate)-Adenosine, 5'-O-(1-Thiophosphate)-Cytidine, 5'-O-(1-Thiophosphate)-Guano sine, 5'-O-(1-Thiophosphate)-Uridine or 5'-O-(1-Thiophosphate)-Pseudouridine.

In further specific embodiments the modified nucleosides include nucleoside modifications selected from 6-aza-cytidine, 2-thio-cytidine, α-thio-cytidine, Pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, Pyrrolo-cytidine, inosine, α-thio-guanosine, 6-methyl-guanosine, 5-methyl-cytdine, 8-oxo-guanosine, 7-deaza-guanosine, N1-methyl-adenosine, 2-amino-6-Chloro-purine, N6-methyl-2-amino-purine, Pseudo-iso-cytidine, 6-Chloro-purine, N6-methyl-adenosine, α-thio-adenosine, 8-azido-adenosine, 7-deaza-adenosine.

Further modified nucleosides have been described previously (WO 2013/052523).

Oxidation status of RNA molecules: Random RNA modifications may occur by oxidation of the RNA molecule through reactive oxygen species which are involved in the killing of bacteria and in cell signaling pathways. More than 20 different purine and pyrimidine modifications formed by reactive oxygen species are known, which include: 8-hydroxyguanosine (8-OHG), which can react further to 8-oxo-7,8-dihydro-2'-deoxyguanosine, dehydroguanidinohyantoin, 2,4,6-trioxo-[1,3,5]triazinane-1-carboxamidine, N-nitro-dehydroguanidinohydantoin, spiroiminodihydantoin, guanidinohydantoin, 4-hydroxy-2,5-dioxo-imidazolidine-4-carboxylic acid, 3-nitrotyrosine, 3.3'-dityrosine, 3-hydroxy-5-imino-3,3a,4,5-tetrahydro-1H-imidazo[4,5-d]imidazol-2-one, parabanic acid, cyanuric acid, 4-hydroxy-8-oxo-4,8-dihydro-2'-desoxyguanosine, 4,5-dihydro-5-hydroxy-4-(nitrosooxy)-2-desoxyguanosine, 2-amino-5[(2-deoxy-β-D-erythro-pentofuranpsyl)amino]-4H-imidazol-4-one, 2,2-diamino-4-[(2-deoxy-β-D-erythro-pentofuranpsyl)amino]-5-(2H)-oxazolone, 5-[hydroxymethyl]-uracil, 2-thiobarbituric acid, 8-nitroguanine, hypoxanthine, uracil, thymine and xanthine.

Determining the percentage of modified nucleosides that arise from oxidation in an RNA molecule will therefore provide information on the oxidation status of the RNA molecules. The most prominent oxidative modification is 8-hydroxyguanosine. Of note, 8-OHG modifications in mRNA lead to reduced protein levels and altered protein function due to ribosome stalling (Shan et al. (2007) FASEB J. 21: 2753-2764). Interestingly, age-associated oxidative damage to RNA has been demonstrated in neurons and may play a role in neurodegeneration and other diseases (Nunomura et al. (2012) Neurotox. Res. 22: 231-248).

Chemical synthesis of RNA: Chemical synthesis of relatively short fragments of oligonucleotides with defined, known chemical structure provides a rapid and inexpensive access to custom-made oligonucleotides of any desired sequence. Whereas enzymes synthesize DNA and RNA only in the 5' to 3' direction, chemical oligonucleotide synthesis does not have this limitation, although it is most often carried out in the opposite, i.e. the 3' to 5' direction. Currently, the process is implemented as solid-phase synthesis using the phosphoramidite method and phosphoramidite building blocks derived from protected nucleosides (A, C, G, and U), or chemically modified nucleosides.

To obtain the desired oligonucleotide, the building blocks are sequentially coupled to the growing oligonucleotide chain on a solid phase in the order required by the sequence of the product in a fully automated process. Upon the completion of the chain assembly, the product is released from the solid phase to the solution, deprotected, and collected. The occurrence of side reactions sets practical limits for the length of synthetic oligonucleotides (up to about 200 nucleotide residues), because the number of errors increases with the length of the oligonucleotide being synthesized. Products are often isolated by HPLC to obtain the desired oligonucleotides in high purity.

Chemically synthesized oligonucleotides find a variety of applications in molecular biology and medicine. They are most commonly used as antisense oligonucleotides, small interfering RNA, primers for DNA sequencing and amplification, probes for detecting complementary DNA or RNA via molecular hybridization, tools for the targeted introduction of mutations and restriction sites, and for the synthesis of artificial genes.

In vitro transcription: The terms "in vitro transcription" or "RNA in vitro transcription" relate to a process wherein RNA is synthesized in a cell-free system (in vitro). DNA, particularly plasmid DNA, is used as template of known sequence and length for the generation of RNA transcripts. RNA may be obtained by DNA-dependent in vitro transcription of an appropriate DNA template, which according to the present invention is preferably a linearized plasmid DNA template. The promoter for controlling in vitro transcription can be any promoter for any DNA-dependent RNA polymerase. Particular examples of DNA-dependent RNA polymerases are the T7, T3, and SP6 RNA polymerases. A DNA template for in vitro RNA transcription may be obtained by cloning of a nucleic acid, in particular cDNA corresponding to the respective RNA to be in vitro transcribed, and introducing it into an appropriate vector for in vitro transcription, for example into plasmid DNA. In a preferred embodiment of the present invention the DNA template is linearized with a suitable restriction enzyme, before it is transcribed in vitro. The cDNA may be obtained by reverse transcription of mRNA or chemical synthesis. Moreover, the DNA template for in vitro RNA synthesis may also be obtained by gene synthesis.

Methods for in vitro transcription are known in the art (see, e.g., Geall et al. (2013) Semin. Immunol. 25(2): 152-159; Brunelle et al. (2013) Methods Enzymol. 530:101-14). Reagents used in said method typically include:

1) a linearized DNA template with a promoter sequence that has a high binding affinity for its respective RNA polymerase such as bacteriophage-encoded RNA polymerases;

2) ribonucleoside triphosphates (NTPs) for the four bases (adenine, cytosine, guanine and uracil);
3) optionally a cap analogue as defined above (e.g. m7G(5')ppp(5')G (m7G));
4) a DNA-dependent RNA polymerase capable of binding to the promoter sequence within the linearized DNA template (e.g. T7, T3 or SP6 RNA polymerase);
5) optionally a ribonuclease (RNase) inhibitor to inactivate any contaminating RNase;
6) optionally a pyrophosphatase to degrade pyrophosphate, which may inhibit transcription;
7) $MgCl_2$, which supplies $Mg^{2+}$ ions as a co-factor for the polymerase;
8) a buffer to maintain a suitable pH value, which can also contain antioxidants (e.g. DTT), and/or polyamines such as spermidine at optimal concentrations.

Purification/purifying: The terms "purification", "purified" or "purifying" are intended to mean that the target RNA is separated and/or isolated from the by-products and the components of the RNA production (e.g. chemical synthesis, RNA in vitro transcription). In the context of RNA in vitro transcription, the target RNA is separated and/or isolated from the by-products and the components of the RNA in vitro transcription reaction present in the sample comprising the target RNA after the RNA in vitro transcription reaction. Thus, after purification the purified target RNA sample has a higher purity than the target RNA-containing sample prior to purification, i.e. the amount of by-products and the components of the RNA in vitro transcription reaction is lower than in the sample after transcription, but before purification. Undesired constituents of RNA-containing samples which therefore need to be separated may in particular be by-products of the RNA in vitro transcription reaction, or also excessively long transcripts, if plasmids are not completely linearized. In addition, components of the RNA in vitro transcription reaction mixture, such as enzymes, for example RNases and polymerases, and nucleotides may be separated from the target RNA in the purification step.

After the purification step, the target RNA has a higher purity than before the purification step, but may still contain by-products which may be detected by the method of the present invention. The degree of purity after the purification step may be more than 70% or 75%, in particular more than 80% or 85%, very particularly more than 90% or 95% and most favorably 99% or more. The degree of purity may for example be determined by an analytical HPLC, wherein the area of the peak for the target RNA is related to the total area of all peaks representing the by-products.

Nucleoside standards: To be able to identify the compound eluted in any HPLC peak, standards are run under the same conditions, which allows for peak alignment between the sample and the standard, provided that the eluted compound corresponds to one in a standard sample. For the identification of nucleosides or modified nucleosides in an RNA molecule, standards of nucleosides that have been treated in the same way as the sample are run in parallel to the RNA molecule. Furthermore, using different concentrations of each nucleoside standard allows for correlation of the peak area with the amount of nucleoside in the sample.

Nucleoside: Nucleosides are glycosylamines that correspond to nucleotides without a phosphate group. A nucleoside consists simply of a nucleobase (also termed a nitrogenous base) and a 5-carbon sugar (either ribose or deoxyribose), whereas a nucleotide is composed of a nucleobase, a five-carbon sugar, and one or more phosphate groups. In a nucleoside, the base is bound to either ribose or deoxyribose via a beta-glycosidic linkage. Examples of nucleosides include cytidine, uridine, adenosine, guanosine, thymidine and inosine.

Expected sequence: The expected sequence of an RNA molecule is the nucleotide sequence predicted from the sequence of the DNA template from which it is transcribed in the process of RNA in vitro transcription, or the order of synthesis steps in its chemical synthesis protocol, i.e. the nucleotide sequence with which any sequence of an actually produced molecule will be compared during quality control.

Measured content: The measured content of a nucleoside is the actual content of said nucleoside in an in vitro transcribed RNA molecule or chemically synthesized RNA molecule. Within the present invention, the measured content is determined by HPLC analysis of the nucleoside ratios of the hydrolyzed RNA molecules.

Expected ratio: The expected ratio of a nucleoside is the number of this nucleoside in the expected sequence of an RNA molecule divided by the total number of all nucleosides in the expected sequence.

Measured ratio: The measured ratio of a nucleoside is the number of this nucleoside detected in in vitro transcribed or chemically synthesized RNA molecules divided by the total number of nucleosides detected in said RNA molecules.

DETAILED DESCRIPTION OF THE INVENTION

As discussed above, the present invention relates to the field of RNA analysis, specifically to methods for quality control in RNA production.

Accordingly, the present invention relates to a method for analyzing a sample of RNA molecules transcribed from a template DNA with known sequence and length or chemically synthesized with known sequence and length, comprising the steps of:
a) providing a sample comprising RNA molecules;
b) completely hydrolyzing the RNA molecules, thereby releasing nucleosides;
c) separating and quantifying the released nucleosides by HPLC;
d) determining at least one of:
the number of copies of the RNA molecules in the sample,
the matching of the sequence of the RNA molecules with the known sequence,
the matching of the length of the RNA molecules with the known length,
the capping degree of the RNA molecules within the sample, and
the length of homopolymeric elements in the RNA molecules.

In one embodiment, the method further comprises determining in step d) at least one of:
the incorporation and amount of modified nucleotides into the RNA molecules, and
the oxidation status of the RNA molecules.

In a preferred embodiment, the method comprises determining all of:
the number of copies of the RNA molecules in the sample,
the matching of the sequence of the RNA molecules with the known sequence,
the matching of the length of the RNA molecules with the known length,
the capping degree of the RNA molecules within the sample, the length of homopolymeric elements, preferably including the poly(A) tail, in the RNA molecules,
the incorporation and amount of modified nucleotides into the RNA molecules, and
the oxidation status of the RNA molecules.

In another embodiment, the method comprises determining all of:
the number of copies of the RNA molecules in the sample, and
the matching of the sequence of the RNA molecules with the known sequence.

In another embodiment, the method comprises determining all of:
the number of copies of the RNA molecules in the sample,
the matching of the sequence of the RNA molecules with the known sequence, and
the matching of the length of the RNA molecules with the known length.

In another embodiment, the method comprises determining all of:
the number of copies of the RNA molecules in the sample,
the matching of the sequence of the RNA molecules with the known sequence,
the matching of the length of the RNA molecules with the known length, and
the capping degree of the RNA molecules within the sample.

In another embodiment, the method comprises determining all of:
the number of copies of the RNA molecules in the sample,
the matching of the sequence of the RNA molecules with the known sequence,
the matching of the length of the RNA molecules with the known length,
the capping degree of the RNA molecules within the sample, and
the length of homopolymeric elements, preferably including the poly(A) tail, in the RNA molecules.

In another embodiment, the method comprises determining all of:
the number of copies of the RNA molecules in the sample,
the matching of the sequence of the RNA molecules with the known sequence,
the matching of the length of the RNA molecules with the known length,
the capping degree of the RNA molecules within the sample,
the length of homopolymeric elements, preferably including the poly(A) tail, in the RNA molecules, and
the incorporation and amount of modified nucleotides into the RNA molecules.

In another embodiment, the method comprises determining all of:
the number of copies of the RNA molecules in the sample,
the matching of the sequence of the RNA molecules with the known sequence, and
the capping degree of the RNA molecules within the sample.

In another embodiment, the method comprises determining all of:
the number of copies of the RNA molecules in the sample,
the matching of the sequence of the RNA molecules with the known sequence,
the capping degree of the RNA molecules within the sample, and
the length of homopolymeric elements, preferably including the poly(A) tail, in the RNA molecules.

In another embodiment, the method comprises determining all of:
the number of copies of the RNA molecules in the sample,
the matching of the sequence of the RNA molecules with the known sequence,
the capping degree of the RNA molecules within the sample,
the length of homopolymeric elements, preferably including the poly(A) tail, in the RNA molecules, and
the incorporation and amount of modified nucleotides into the RNA molecules.

In another embodiment, the method comprises determining all of:
the number of copies of the RNA molecules in the sample,
the matching of the sequence of the RNA molecules with the known sequence,
the capping degree of the RNA molecules within the sample,
the length of homopolymeric elements, preferably including the poly(A) tail, in the RNA molecules,
the incorporation and amount of modified nucleotides into the RNA molecules, and
the oxidation status of the RNA molecules.

In another embodiment, the method comprises determining all of:
the number of copies of the RNA molecules in the sample,
the matching of the sequence of the RNA molecules with the known sequence, and
the length of homopolymeric elements, preferably including the poly(A) tail, in the RNA molecules.

In another embodiment, the method comprises determining all of:
the number of copies of the RNA molecules in the sample,
the matching of the sequence of the RNA molecules with the known sequence,
the length of homopolymeric elements, preferably including the poly(A) tail, in the RNA molecules, and
the incorporation and amount of modified nucleotides into the RNA molecules.

In another embodiment, the method comprises determining all of:
the number of copies of the RNA molecules in the sample,
the matching of the sequence of the RNA molecules with the known sequence,
the length of homopolymeric elements, preferably including the poly(A) tail, in the RNA molecules,
the incorporation and amount of modified nucleotides into the RNA molecules, and
the oxidation status of the RNA molecules.

In another embodiment, the method comprises determining all of:
the number of copies of the RNA molecules in the sample,
the matching of the sequence of the RNA molecules with the known sequence, and
the incorporation and amount of modified nucleotides into the RNA molecules.

In another embodiment, the method comprises determining all of:
the number of copies of the RNA molecules in the sample,
the matching of the sequence of the RNA molecules with the known sequence,
the incorporation and amount of modified nucleotides into the RNA molecules, and
the oxidation status of the RNA molecules.

In another embodiment, the method comprises determining all of:
the number of copies of the RNA molecules in the sample,
the matching of the sequence of the RNA molecules with the known sequence, and
the oxidation status of the RNA molecules.

In another embodiment, the method comprises determining all of:
- the number of copies of the RNA molecules in the sample, and
- the matching of the length of the RNA molecules with the known length.

In another embodiment, the method comprises determining all of:
- the number of copies of the RNA molecules in the sample,
- the matching of the length of the RNA molecules with the known length, and
- the capping degree of the RNA molecules within the sample.

In another embodiment, the method comprises determining all of:
- the number of copies of the RNA molecules in the sample,
- the matching of the length of the RNA molecules with the known length,
- the capping degree of the RNA molecules within the sample, and
- the length of homopolymeric elements, preferably including the poly(A) tail, in the RNA molecules.

In another embodiment, the method comprises determining all of:
- the number of copies of the RNA molecules in the sample,
- the matching of the length of the RNA molecules with the known length,
- the capping degree of the RNA molecules within the sample,
- the length of homopolymeric elements, preferably including the poly(A) tail, in the RNA molecules, and
- the incorporation and amount of modified nucleotides into the RNA molecules.

In another embodiment, the method comprises determining all of:
- the number of copies of the RNA molecules in the sample,
- the matching of the length of the RNA molecules with the known length,
- the capping degree of the RNA molecules within the sample,
- the length of homopolymeric elements, preferably including the poly(A) tail, in the RNA molecules,
- the incorporation and amount of modified nucleotides into the RNA molecules, and
- the oxidation status of the RNA molecules.

In another embodiment, the method comprises determining all of:
- the number of copies of the RNA molecules in the sample,
- the matching of the length of the RNA molecules with the known length, and
- the length of homopolymeric elements, preferably including the poly(A) tail, in the RNA molecules.

In another embodiment, the method comprises determining all of:
- the number of copies of the RNA molecules in the sample,
- the matching of the length of the RNA molecules with the known length,
- the length of homopolymeric elements, preferably including the poly(A) tail, in the RNA molecules, and
- the incorporation and amount of modified nucleotides into the RNA molecules.

In another embodiment, the method comprises determining all of:
- the number of copies of the RNA molecules in the sample,
- the matching of the length of the RNA molecules with the known length,
- the length of homopolymeric elements, preferably including the poly(A) tail, in the RNA molecules,
- the incorporation and amount of modified nucleotides into the RNA molecules, and
- the oxidation status of the RNA molecules.

In another embodiment, the method comprises determining all of:
- the number of copies of the RNA molecules in the sample,
- the matching of the length of the RNA molecules with the known length, and
- the incorporation and amount of modified nucleotides into the RNA molecules.

In another embodiment, the method comprises determining all of:
- the number of copies of the RNA molecules in the sample,
- the matching of the length of the RNA molecules with the known length,
- the incorporation and amount of modified nucleotides into the RNA molecules, and
- the oxidation status of the RNA molecules.

In another embodiment, the method comprises determining all of:
- the number of copies of the RNA molecules in the sample,
- the matching of the length of the RNA molecules with the known length, and
- the oxidation status of the RNA molecules.

In another embodiment, the method comprises determining all of:
- the number of copies of the RNA molecules in the sample, and
- the capping degree of the RNA molecules within the sample.

In another embodiment, the method comprises determining all of:
- the number of copies of the RNA molecules in the sample,
- the capping degree of the RNA molecules within the sample, and
- the length of homopolymeric elements, preferably including the poly(A) tail, in the RNA molecules.

In another embodiment, the method comprises determining all of:
- the number of copies of the RNA molecules in the sample,
- the capping degree of the RNA molecules within the sample,
- the length of homopolymeric elements, preferably including the poly(A) tail, in the RNA molecules, and
- the incorporation and amount of modified nucleotides into the RNA molecules.

In another embodiment, the method comprises determining all of:
- the number of copies of the RNA molecules in the sample,
- the capping degree of the RNA molecules within the sample,
- the length of homopolymeric elements, preferably including the poly(A) tail, in the RNA molecules,
- the incorporation and amount of modified nucleotides into the RNA molecules, and
- the oxidation status of the RNA molecules.

In another embodiment, the method comprises determining all of:
- the number of copies of the RNA molecules in the sample,
- the capping degree of the RNA molecules within the sample, and
- the incorporation and amount of modified nucleotides into the RNA molecules.

In another embodiment, the method comprises determining all of:

the number of copies of the RNA molecules in the sample,
the capping degree of the RNA molecules within the sample,
the incorporation and amount of modified nucleotides into the RNA molecules, and
the oxidation status of the RNA molecules.

In another embodiment, the method comprises determining all of:
the number of copies of the RNA molecules in the sample,
the capping degree of the RNA molecules within the sample, and
the oxidation status of the RNA molecules.

In another embodiment, the method comprises determining all of:
the number of copies of the RNA molecules in the sample, and
the length of homopolymeric elements, preferably including the poly(A) tail, in the RNA molecules.

In another embodiment, the method comprises determining all of:
the number of copies of the RNA molecules in the sample,
the length of homopolymeric elements, preferably including the poly(A) tail, in the RNA molecules, and
the incorporation and amount of modified nucleotides into the RNA molecules.

In another embodiment, the method comprises determining all of:
the number of copies of the RNA molecules in the sample,
the length of homopolymeric elements, preferably including the poly(A) tail, in the RNA molecules,
the incorporation and amount of modified nucleotides into the RNA molecules, and
the oxidation status of the RNA molecules.

In another embodiment, the method comprises determining all of:
the number of copies of the RNA molecules in the sample,
the length of homopolymeric elements, preferably including the poly(A) tail, in the RNA molecules, and
the oxidation status of the RNA molecules.

In another embodiment, the method comprises determining all of:
the number of copies of the RNA molecules in the sample, and
the incorporation and amount of modified nucleotides into the RNA molecules.

In another embodiment, the method comprises determining all of:
the number of copies of the RNA molecules in the sample,
the incorporation and amount of modified nucleotides into the RNA molecules, and
the oxidation status of the RNA molecules.

In another embodiment, the method comprises determining all of:
the number of copies of the RNA molecules in the sample, and
the oxidation status of the RNA molecules.

In one embodiment, the method comprises determining all of:
the matching of the sequence of the RNA molecules with the known sequence, and
the matching of the length of the RNA molecules with the known length.

In one embodiment, the method comprises determining all of:
the matching of the sequence of the RNA molecules with the known sequence,
the matching of the length of the RNA molecules with the known length, and
the capping degree of the RNA molecules within the sample.

In one embodiment, the method comprises determining all of:
the matching of the sequence of the RNA molecules with the known sequence,
the matching of the length of the RNA molecules with the known length,
the capping degree of the RNA molecules within the sample, and
the length of homopolymeric elements, preferably including the poly(A) tail, in the RNA molecules.

In one embodiment, the method comprises determining all of:
the matching of the sequence of the RNA molecules with the known sequence,
the matching of the length of the RNA molecules with the known length,
the capping degree of the RNA molecules within the sample,
the length of homopolymeric elements, preferably including the poly(A) tail, in the RNA molecules, and
the incorporation and amount of modified nucleotides into the RNA molecules.

In one embodiment, the method comprises determining all of:
the matching of the sequence of the RNA molecules with the known sequence,
the matching of the length of the RNA molecules with the known length,
the capping degree of the RNA molecules within the sample,
the length of homopolymeric elements, preferably including the poly(A) tail, in the RNA molecules,
the incorporation and amount of modified nucleotides into the RNA molecules, and
the oxidation status of the RNA molecules.

In another embodiment, the method comprises determining all of:
the matching of the sequence of the RNA molecules with the known sequence,
the matching of the length of the RNA molecules with the known length, and
the length of homopolymeric elements, preferably including the poly(A) tail, in the RNA molecules.

In another embodiment, the method comprises determining all of:
the matching of the sequence of the RNA molecules with the known sequence,
the matching of the length of the RNA molecules with the known length,
the length of homopolymeric elements, preferably including the poly(A) tail, in the RNA molecules, and
the incorporation and amount of modified nucleotides into the RNA molecules.

In another embodiment, the method comprises determining all of:
the matching of the sequence of the RNA molecules with the known sequence,
the matching of the length of the RNA molecules with the known length,
the length of homopolymeric elements, preferably including the poly(A) tail, in the RNA molecules,
the incorporation and amount of modified nucleotides into the RNA molecules, and the oxidation status of the RNA molecules.

In another embodiment, the method comprises determining all of:
the matching of the sequence of the RNA molecules with the known sequence,
the matching of the length of the RNA molecules with the known length, and
the incorporation and amount of modified nucleotides into the RNA molecules.

In another embodiment, the method comprises determining all of:
the matching of the sequence of the RNA molecules with the known sequence,
the matching of the length of the RNA molecules with the known length,
the incorporation and amount of modified nucleotides into the RNA molecules, and
the oxidation status of the RNA molecules.

In another embodiment, the method comprises determining all of:
the matching of the sequence of the RNA molecules with the known sequence,
the matching of the length of the RNA molecules with the known length, and
the oxidation status of the RNA molecules.

In one embodiment, the method comprises determining all of:
the matching of the sequence of the RNA molecules with the known sequence, and
the capping degree of the RNA molecules within the sample.

In one embodiment, the method comprises determining all of:
the matching of the sequence of the RNA molecules with the known sequence,
the capping degree of the RNA molecules within the sample, and
the length of homopolymeric elements, preferably including the poly(A) tail, in the RNA molecules.

In one embodiment, the method comprises determining all of:
the matching of the sequence of the RNA molecules with the known sequence,
the capping degree of the RNA molecules within the sample,
the length of homopolymeric elements, preferably including the poly(A) tail, in the RNA molecules, and
the incorporation and amount of modified nucleotides into the RNA molecules.

In one embodiment, the method comprises determining all of:
the matching of the sequence of the RNA molecules with the known sequence,
the capping degree of the RNA molecules within the sample,
the length of homopolymeric elements, preferably including the poly(A) tail, in the RNA molecules,
the incorporation and amount of modified nucleotides into the RNA molecules, and
the oxidation status of the RNA molecules.

In one embodiment, the method comprises determining all of:
the matching of the sequence of the RNA molecules with the known sequence,
the capping degree of the RNA molecules within the sample, and
the incorporation and amount of modified nucleotides into the RNA molecule.

In one embodiment, the method comprises determining all of:
the matching of the sequence of the RNA molecules with the known sequence,
the capping degree of the RNA molecules within the sample,
the incorporation and amount of modified nucleotides into the RNA molecules, and
the oxidation status of the RNA molecules.

In one embodiment, the method comprises determining all of:
the matching of the sequence of the RNA molecules with the known sequence,
the capping degree of the RNA molecules within the sample, and
the oxidation status of the RNA molecules.

In one embodiment, the method comprises determining all of:
the matching of the sequence of the RNA molecules with the known sequence, and
the length of homopolymeric elements, preferably including the poly(A) tail, in the RNA molecules.

In one embodiment, the method comprises determining all of:
the matching of the sequence of the RNA molecules with the known sequence,
the length of homopolymeric elements, preferably including the poly(A) tail, in the RNA molecules, and
the incorporation and amount of modified nucleotides into the RNA molecules.

In one embodiment, the method comprises determining all of:
the matching of the sequence of the RNA molecules with the known sequence,
the length of homopolymeric elements, preferably including the poly(A) tail, in the RNA molecules,
the incorporation and amount of modified nucleotides into the RNA molecules, and
the oxidation status of the RNA molecules.

In one embodiment, the method comprises determining all of:
the matching of the sequence of the RNA molecules with the known sequence,
the length of homopolymeric elements, preferably including the poly(A) tail, in the RNA molecules, and
the oxidation status of the RNA molecules.

In another embodiment, the method comprises determining all of:
the matching of the sequence of the RNA molecules with the known sequence, and
the incorporation and amount of modified nucleotides into the RNA molecules.

In another embodiment, the method comprises determining all of:
the matching of the sequence of the RNA molecules with the known sequence,
the incorporation and amount of modified nucleotides into the RNA molecules, and
the oxidation status of the RNA molecules.

In another embodiment, the method comprises determining all of:
the matching of the sequence of the RNA molecules with the known sequence, and
the oxidation status of the RNA molecules.

In another embodiment, the method comprises determining all of:
- the matching of the length of the RNA molecules with the known length, and
- the capping degree of the RNA molecules within the sample.

In another embodiment, the method comprises determining all of:
- the matching of the length of the RNA molecules with the known length,
- the capping degree of the RNA molecules within the sample, and
- the length of homopolymeric elements, preferably including the poly(A) tail, in the RNA molecules.

In another embodiment, the method comprises determining all of:
- the matching of the length of the RNA molecules with the known length,
- the capping degree of the RNA molecules within the sample,
- the length of homopolymeric elements, preferably including the poly(A) tail, in the RNA molecules, and
- the incorporation and amount of modified nucleotides into the RNA molecules.

In another embodiment, the method comprises determining all of:
- the matching of the length of the RNA molecules with the known length,
- the capping degree of the RNA molecules within the sample,
- the length of homopolymeric elements, preferably including the poly(A) tail, in the RNA molecules,
- the incorporation and amount of modified nucleotides into the RNA molecules, and
- the oxidation status of the RNA molecules.

In another embodiment, the method comprises determining all of:
- the matching of the length of the RNA molecules with the known length,
- the capping degree of the RNA molecules within the sample, and
- the incorporation and amount of modified nucleotides into the RNA molecules.

In another embodiment, the method comprises determining all of:
- the matching of the length of the RNA molecules with the known length,
- the capping degree of the RNA molecules within the sample,
- the incorporation and amount of modified nucleotides into the RNA molecules, and
- the oxidation status of the RNA molecules.

In another embodiment, the method comprises determining all of:
- the matching of the length of the RNA molecules with the known length,
- the capping degree of the RNA molecules within the sample, and
- the oxidation status of the RNA molecules.

In another embodiment, the method comprises determining all of:
- the matching of the length of the RNA molecules with the known length, and
- the length of homopolymeric elements, preferably including the poly(A) tail, in the RNA molecules.

In another embodiment, the method comprises determining all of:
- the matching of the length of the RNA molecules with the known length,
- the length of homopolymeric elements, preferably including the poly(A) tail, in the RNA molecules, and
- the incorporation and amount of modified nucleotides into the RNA molecules.

In another embodiment, the method comprises determining all of:
- the matching of the length of the RNA molecules with the known length,
- the length of homopolymeric elements, preferably including the poly(A) tail, in the RNA molecules,
- the incorporation and amount of modified nucleotides into the RNA molecules, and
- the oxidation status of the RNA molecules.

In another embodiment, the method comprises determining all of:
- the matching of the length of the RNA molecules with the known length,
- the length of homopolymeric elements, preferably including the poly(A) tail, in the RNA molecules, and
- the oxidation status of the RNA molecules.

In another embodiment, the method comprises determining all of:
- the matching of the length of the RNA molecules with the known length, and
- the incorporation and amount of modified nucleotides into the RNA molecules.

In another embodiment, the method comprises determining all of:
- the matching of the length of the RNA molecules with the known length,
- the incorporation and amount of modified nucleotides into the RNA molecules, and
- the oxidation status of the RNA molecules.

In another embodiment, the method comprises determining all of:
- the matching of the length of the RNA molecules with the known length, and
- the oxidation status of the RNA molecules.

In another embodiment, the method comprises determining all of:
- the capping degree of the RNA molecules within the sample, and
- the length of homopolymeric elements, preferably including the poly(A) tail, in the RNA molecules.

In another embodiment, the method comprises determining all of:
- the capping degree of the RNA molecules within the sample,
- the length of homopolymeric elements, preferably including the poly(A) tail, in the RNA molecules, and
- the incorporation and amount of modified nucleotides into the RNA molecules.

In another embodiment, the method comprises determining all of:
- the capping degree of the RNA molecules within the sample,
- the length of homopolymeric elements, preferably including the poly(A) tail, in the RNA molecules,
- the incorporation and amount of modified nucleotides into the RNA molecules, and
- the oxidation status of the RNA molecules.

In another embodiment, the method comprises determining all of:
- the capping degree of the RNA molecules within the sample, the length of homopolymeric elements, preferably including the poly(A) tail, in the RNA molecules, and
the oxidation status of the RNA molecules.
In another embodiment, the method comprises determining all of:
the capping degree of the RNA molecules within the sample, and
the incorporation and amount of modified nucleotides into the RNA molecules.
In another embodiment, the method comprises determining all of:
the capping degree of the RNA molecules within the sample,
the incorporation and amount of modified nucleotides into the RNA molecules, and
the oxidation status of the RNA molecules.
In another embodiment, the method comprises determining all of:
the capping degree of the RNA molecules within the sample, and
the oxidation status of the RNA molecules.
In another embodiment, the method comprises determining all of:
the length of homopolymeric elements, preferably including the poly(A) tail, in the RNA molecules, and
the incorporation and amount of modified nucleotides into the RNA molecules.
In another embodiment, the method comprises determining all of:
the length of homopolymeric elements, preferably including the poly(A) tail, in the RNA molecules,
the incorporation and amount of modified nucleotides into the RNA molecules, and
the oxidation status of the RNA molecules.
In another embodiment, the method comprises determining all of:
the length of homopolymeric elements, preferably including the poly(A) tail, in the RNA molecules, and
the oxidation status of the RNA molecules.
In another embodiment, the method comprises determining all of:
the incorporation and amount of modified nucleotides into the RNA molecules, and
the oxidation status of the RNA molecules.
If the RNA molecules are not mRNA molecules, step d) of the method of the invention may involve the following embodiments:
In one embodiment, the method comprises determining all of:
the number of copies of the RNA molecules in the sample, and
the matching of the sequence of the RNA molecules with the known sequence.
In another embodiment, the method comprises determining all of:
the number of copies of the RNA molecules in the sample,
the matching of the sequence of the RNA molecules with the known sequence, and
the matching of the length of the RNA molecules with the known length.
In another embodiment, the method comprises determining all of:
the number of copies of the RNA molecules in the sample,
the matching of the sequence of the RNA molecules with the known sequence, and
the length of homopolymeric elements in the RNA molecules.

In another embodiment, the method comprises determining all of:
the number of copies of the RNA molecules in the sample,
the matching of the sequence of the RNA molecules with the known sequence,
the length of homopolymeric elements in the RNA molecules, and
the incorporation and amount of modified nucleotides into the RNA molecules.
In another embodiment, the method comprises determining all of:
the number of copies of the RNA molecules in the sample,
the matching of the sequence of the RNA molecules with the known sequence,
the length of homopolymeric elements in the RNA molecules,
the incorporation and amount of modified nucleotides into the RNA molecules, and
the oxidation status of the RNA molecules.
In another embodiment, the method comprises determining all of:
the number of copies of the RNA molecules in the sample,
the matching of the sequence of the RNA molecules with the known sequence, and
the incorporation and amount of modified nucleotides into the RNA molecules.
In another embodiment, the method comprises determining all of:
the number of copies of the RNA molecules in the sample,
the matching of the sequence of the RNA molecules with the known sequence,
the incorporation and amount of modified nucleotides into the RNA molecules, and
the oxidation status of the RNA molecules.
In another embodiment, the method comprises determining all of:
the number of copies of the RNA molecules in the sample,
the matching of the sequence of the RNA molecules with the known sequence, and
the oxidation status of the RNA molecules.
In another embodiment, the method comprises determining all of:
the number of copies of the RNA molecules in the sample, and
the matching of the length of the RNA molecules with the known length.
In another embodiment, the method comprises determining all of:
the number of copies of the RNA molecules in the sample,
the matching of the length of the RNA molecules with the known length, and
the length of homopolymeric elements in the RNA molecules.
In another embodiment, the method comprises determining all of:
the number of copies of the RNA molecules in the sample,
the matching of the length of the RNA molecules with the known length,
the length of homopolymeric elements in the RNA molecules, and
the incorporation and amount of modified nucleotides into the RNA molecules.
In another embodiment, the method comprises determining all of:
the number of copies of the RNA molecules in the sample,
the matching of the length of the RNA molecules with the known length, the length of homopolymeric elements in the RNA molecules, the incorporation and amount of modified nucleotides into the RNA molecules, and the oxidation status of the RNA molecules.

In another embodiment, the method comprises determining all of:

the number of copies of the RNA molecules in the sample, the matching of the length of the RNA molecules with the known length, and the incorporation and amount of modified nucleotides into the RNA molecules.

In another embodiment, the method comprises determining all of:

the number of copies of the RNA molecules in the sample, the matching of the length of the RNA molecules with the known length, the incorporation and amount of modified nucleotides into the RNA molecules, and the oxidation status of the RNA molecules.

In another embodiment, the method comprises determining all of:

the number of copies of the RNA molecules in the sample, the matching of the length of the RNA molecules with the known length, and the oxidation status of the RNA molecules.

In another embodiment, the method comprises determining all of:

the number of copies of the RNA molecules in the sample, and the length of homopolymeric elements in the RNA molecules.

In another embodiment, the method comprises determining all of:

the number of copies of the RNA molecules in the sample, the length of homopolymeric elements in the RNA molecules, and the incorporation and amount of modified nucleotides into the RNA molecules.

In another embodiment, the method comprises determining all of:

the number of copies of the RNA molecules in the sample, the length of homopolymeric elements in the RNA molecules, the incorporation and amount of modified nucleotides into the RNA molecules, and the oxidation status of the RNA molecules.

In another embodiment, the method comprises determining all of:

the number of copies of the RNA molecules in the sample, the length of homopolymeric elements in the RNA molecules, and the oxidation status of the RNA molecules.

In another embodiment, the method comprises determining all of:

the number of copies of the RNA molecules in the sample, and the incorporation and amount of modified nucleotides into the RNA molecules.

In another embodiment, the method comprises determining all of:

the number of copies of the RNA molecules in the sample, the incorporation and amount of modified nucleotides into the RNA molecules, and the oxidation status of the RNA molecules.

In another embodiment, the method comprises determining all of:

the number of copies of the RNA molecules in the sample, and the oxidation status of the RNA molecules.

In one embodiment, the method comprises determining all of:

the matching of the sequence of the RNA molecules with the known sequence, and the matching of the length of the RNA molecules with the known length.

In another embodiment, the method comprises determining all of:

the matching of the sequence of the RNA molecules with the known sequence, the matching of the length of the RNA molecules with the known length, and the length of homopolymeric elements in the RNA molecules.

In another embodiment, the method comprises determining all of:

the matching of the sequence of the RNA molecules with the known sequence, the matching of the length of the RNA molecules with the known length, the length of homopolymeric elements in the RNA molecules, and the incorporation and amount of modified nucleotides into the RNA molecules.

In another embodiment, the method comprises determining all of:

the matching of the sequence of the RNA molecules with the known sequence, the matching of the length of the RNA molecules with the known length, the length of homopolymeric elements in the RNA molecules, the incorporation and amount of modified nucleotides into the RNA molecules, and the oxidation status of the RNA molecules.

In another embodiment, the method comprises determining all of:

the matching of the sequence of the RNA molecules with the known sequence, the matching of the length of the RNA molecules with the known length, and the incorporation and amount of modified nucleotides into the RNA molecules.

In another embodiment, the method comprises determining all of:

the matching of the sequence of the RNA molecules with the known sequence, the matching of the length of the RNA molecules with the known length, the incorporation and amount of modified nucleotides into the RNA molecules, and the oxidation status of the RNA molecules.

In another embodiment, the method comprises determining all of:

the matching of the sequence of the RNA molecules with the known sequence, the matching of the length of the RNA molecules with the known length, and the oxidation status of the RNA molecules.

In one embodiment, the method comprises determining all of:
- the matching of the sequence of the RNA molecules with the known sequence, and
- the length of homopolymeric elements in the RNA molecules.

In one embodiment, the method comprises determining all of:
- the matching of the sequence of the RNA molecules with the known sequence,
- the length of homopolymeric elements in the RNA molecules, and
- the incorporation and amount of modified nucleotides into the RNA molecules.

In one embodiment, the method comprises determining all of:
- the matching of the sequence of the RNA molecules with the known sequence,
- the length of homopolymeric elements in the RNA molecules,
- the incorporation and amount of modified nucleotides into the RNA molecules, and
- the oxidation status of the RNA molecules.

In one embodiment, the method comprises determining all of:
- the matching of the sequence of the RNA molecules with the known sequence,
- the length of homopolymeric elements in the RNA molecules, and
- the oxidation status of the RNA molecules.

In another embodiment, the method comprises determining all of:
- the matching of the sequence of the RNA molecules with the known sequence, and
- the incorporation and amount of modified nucleotides into the RNA molecules.

In another embodiment, the method comprises determining all of:
- the matching of the sequence of the RNA molecules with the known sequence,
- the incorporation and amount of modified nucleotides into the RNA molecules, and
- the oxidation status of the RNA molecules.

In another embodiment, the method comprises determining all of:
- the matching of the sequence of the RNA molecules with the known sequence, and
- the oxidation status of the RNA molecules.

In another embodiment, the method comprises determining all of:
- the matching of the length of the RNA molecules with the known length, and
- the length of homopolymeric elements in the RNA molecules.

In another embodiment, the method comprises determining all of:
- the matching of the length of the RNA molecules with the known length,
- the length of homopolymeric elements in the RNA molecules, and
- the incorporation and amount of modified nucleotides into the RNA molecules.

In another embodiment, the method comprises determining all of:
- the matching of the length of the RNA molecules with the known length,
- the length of homopolymeric elements in the RNA molecules,
- the incorporation and amount of modified nucleotides into the RNA molecules, and
- the oxidation status of the RNA molecules.

In another embodiment, the method comprises determining all of:
- the matching of the length of the RNA molecules with the known length,
- the length of homopolymeric elements in the RNA molecules, and
- the oxidation status of the RNA molecules.

In another embodiment, the method comprises determining all of:
- the matching of the length of the RNA molecules with the known length, and
- the incorporation and amount of modified nucleotides into the RNA molecules.

In another embodiment, the method comprises determining all of:
- the matching of the length of the RNA molecules with the known length,
- the incorporation and amount of modified nucleotides into the RNA molecules, and
- the oxidation status of the RNA molecules.

In another embodiment, the method comprises determining all of:
- the matching of the length of the RNA molecules with the known length, and
- the oxidation status of the RNA molecules.

In another embodiment, the method comprises determining all of:
- the length of homopolymeric elements in the RNA molecules, and
- the incorporation and amount of modified nucleotides into the RNA molecules.

In another embodiment, the method comprises determining all of:
- the length of homopolymeric elements in the RNA molecules,
- the incorporation and amount of modified nucleotides into the RNA molecules, and
- the oxidation status of the RNA molecules.

In another embodiment, the method comprises determining all of:
- the length of homopolymeric elements in the RNA molecules, and
- the oxidation status of the RNA molecules.

In another embodiment, the method comprises determining all of:
- the incorporation and amount of modified nucleotides into the RNA molecules, and
- the oxidation status of the RNA molecules.

Before completely hydrolyzing the RNA molecules, they may be purified, in particular if the RNA molecules are provided by RNA in vitro transcription. In this case, the purification step removes free nucleotides which were not incorporated into the RNA molecules and which may distort the analysis of the nucleosides released by the hydrolysis step.

The RNA molecules may be purified by any suitable method. The method for purifying the RNA molecules is chosen so that the reagents (such as nucleotides and RNA polymerase) and by-products of the RNA in vitro transcription reaction are removed from the sample as completely as possible. Suitable purification methods include alcoholic precipitation, LiCl precipitation, HPLC such as reversed-phase HPLC, anion exchange chromatography, hydroxyapatite chromatography and core bead chromatography, tangential flow filtration, gel filtration chromatography, silica membranes such as, for example, PureYield™ RNA Midiprep System of Promega and affinity chromatography (if a tag is attached to the target RNA or via oligod(T), if the RNA is polyadenylated). Preferably, the target RNA is purified using reversed-phase HPLC.

The HPLC for purifying the RNA is preferably performed on a preparative scale in which relatively large quantities of RNA are purified. Such relatively large quantities are for example quantities of 0.5 mg or more, in particular 1.0 mg to 1000 mg or more, very particularly approximately 1.5 mg or more, upscaling even to the kg range being possible. The above statements are to be understood to mean that these quantities relate to a single HPLC run. If a plurality of HPLC runs is performed, the quantity increases in direct proportion to the number of HPLC runs.

A particularly preferred method for purifying the target RNA is disclosed in WO 2008/077592 A1 and involves a reversed-phase HPLC using a porous reversed phase as stationary phase.

In general, any material known to be used as reverse phase stationary phase, in particular any polymeric material may be used for the inventive method, if that material can be provided in porous form. The stationary phase may be composed of organic and/or inorganic material. Examples for polymers to be used for the purification step of the present invention are (non-alkylated) polystyrenes, (non-alkylated) polystyrenedivinylbenzenes, silica gel, silica gel modified with non-polar residues, particularly silica gel modified with alkyl containing residues, more preferably with butyl-, octyl and/or octadecyl containing residues, silica gel modified with phenylic residues, polymethacrylates, etc.

In a particularly preferred embodiment, the material for the reversed phase is a porous polystyrene polymer, a (non-alkylated) porous polystyrenedivinylbenzene polymer, porous silica gel, porous silica gel modified with non-polar residues, particularly porous silica gel modified with alkyl containing residues, more preferably with butyl-, octyl and/or octadecyl containing residues, porous silica gel modified with phenylic residues, porous polymethacrylates, wherein in particular a porous polystyrene polymer or a non-alkylated (porous) polystyrenedivinylbenzene may be used.

A non-alkylated porous polystyrenedivinylbenzene which is very particularly preferred for the purification step of the method according to the invention is one which, without being limited thereto, may have a particle size of 8.0±1.5 μm, in particular 8.0±0.5 μm, and a pore size of 1000-1500 Å, in particular 1000-1200 Å or 3500-4500 Å.

The stationary phase is conventionally located in a column. V2A steel is conventionally used as the material for the column, but other materials may also be used for the column provided they are suitable for the conditions prevailing during HPLC. Conventionally the column is straight. It is favourable for the HPLC column to have a length of 5 cm to 100 cm and a diameter of 4 mm to 25 mm. Columns used for the purification step of the method of the invention may in particular have the following dimensions: 50 mm long and 7.5 mm in diameter or 50 mm long and 4.6 mm in diameter, or 50 mm long and 10 mm in diameter or any other dimension with regard to length and diameter, which is suitable for preparative recovery of RNA, even lengths of several meters and also larger diameters being feasible in the case of upscaling.

The HPLC is preferably performed as ion-pair, reversed phase HPLC as defined above.

In a preferred embodiment, a mixture of an aqueous solvent and an organic solvent is used as the mobile phase for eluting the RNA. Preferably, the buffer used as the aqueous solvent has a pH of 6.0-8.0, for example of about 7, for example 7.0. More preferably the buffer is triethylammonium acetate which preferably has a concentration of 0.02 M to 0.5 M, more preferably of 0.08 M to 0.12 M. Most preferably, a 0.1 M triethylammonium acetate buffer is used, which also acts as a counter ion to the RNA in the ion pair method.

In a preferred embodiment, the organic solvent which is used in the mobile phase is selected from acetonitrile, methanol, ethanol, 1-propanol, 2-propanol and acetone or a mixture thereof. More preferably it is acetonitrile.

In a particularly preferred embodiment, the mobile phase is a mixture of 0.1 M triethylammonium acetate, pH 7, and acetonitrile.

Preferably, the mobile phase contains 5.0 vol. % to 25.0 vol. % organic solvent, relative to the mobile phase, and for this to be made up to 100 vol. % with the aqueous solvent. Typically, in the event of gradient separation, the proportion of organic solvent is increased, in particular by at least 10%, more preferably by at least 50% and most preferably by at least 100%, optionally by at least 200%, relative to the initial vol. % in the mobile phase. In a preferred embodiment, the proportion of organic solvent in the mobile phase amounts in the course of HPLC separation to 3 to 9, preferably 4 to 7.5, in particular 5.0 vol. %, in each case relative to the mobile phase. More preferably, the proportion of organic solvent in the mobile phase is increased in the course of HPLC separation from 3 to 9, in particular 5.0 vol. % to up to 20.0 vol. %, in each case relative to the mobile phase. Still more preferably, the method is performed in such a way that the proportion of organic solvent in the mobile phase is increased in the course of HPLC separation from 6.5 to 8.5, in particular 7.5 vol. %, to up to 1 7.5 vol. %, in each case relative to the mobile phase.

Even more preferably the mobile phase contains 7.5 vol. % to 17.5 vol. % organic solvent, relative to the mobile phase, and for this to be made up to 100 vol. % with the aqueous buffered solvent.

Elution may proceed isocratically or by means of gradient separation. In isocratic separation, elution of the RNA proceeds with a single eluent or a constant mixture of a plurality of eluents, wherein the solvents described above in detail may be used as eluent.

In a preferred embodiment, gradient separation is performed wherein the composition of the eluent is varied by means of a gradient program. The equipment necessary for gradient separation is known to a person skilled in the art. Gradient elution may here proceed either on the low pressure side by mixing chambers or on the high pressure side by further pumps.

Preferably, the proportion of organic solvent, as described above, is increased relative to the aqueous solvent during gradient separation. The above-described agents may here be used as the aqueous solvent and the likewise above-described agents may be used as the organic solvent. For example, the proportion of organic solvent in the mobile phase may be increased in the course of HPLC separation from 5.0 vol. % to 20.0 vol. %, in each case relative to the mobile phase. In particular, the proportion of organic solvent in the mobile phase may be increased in the course of HPLC separation from 7.5 vol. % to 1 7.5 vol. %, in particular 9.5 to 14.5 vol. %, in each case relative to the mobile phase.

The following gradient program has proven particularly favourable for the purification of RNA:

Eluent A: 0.1 M triethylammonium acetate, pH 7
Eluent B: 0.1 M triethylammonium acetate, pH 7, with 25 vol. % acetonitrile
Eluent Composition:
start: 62% A and 38% B (1 st to 3rd minute)
increase to 58% B (1.67% increase in B per minute), (3rd-15th minute)
100% B (15th to 20th minute)

Another example of a gradient program is described below, the same eluent A and B being used:

Eluent Composition:
starting level: 62% A and 38% B (1 st-3rd min)
separation range I: gradient 38%-49.5% B (5.75% increase in B/min) (3rd-5th min)
separation range II: gradient 49.5%-57% B (0.83% increase in B/min) (5th-14th min)
rinsing range: 100% B (15th-20th min)

It is preferred to use purified solvent for HPLC. Such purified solvents are commercially obtainable. They may additionally also be filtered through a 1 to 5 μm microfilter, which is generally mounted in the system upstream of the pump. It is additionally preferred for all the solvents to be degassed prior to use, since otherwise gas bubbles occur in most pumps. If air bubbles occur in the solvent, they may interfere not only with separation but also with the continuous monitoring of outflow in the detector. The solvents may be degassed by heating, by vigorous stirring with a magnetic stirrer, by brief evacuation, by ultrasonication or by passing a small stream of helium through the solvent storage vessel.

The flow rate of the eluent is selected such that good separation of the RNA from the other constituents contained in the sample to be investigated takes place. The eluent flow rate may amount to from 1 ml/min to several litres per minute (in the case of upscaling), in particular about 1 to 1000 ml/min, more preferably 5 ml to 500 ml/min, even more preferably more than 100 ml/min, depending on the type and scope of the upscaling. This flow rate may be established and regulated by the pump.

Detection proceeds preferably with a UV detector at 254 nm, wherein a reference measurement may be made at 600 nm. However, any other detection method may alternatively be used, with which the RNA may be detected.

For preparative purification of the RNA, it is advisable to collect the RNA-containing eluted solvent quantities. In this respect, it is preferred to carry out this collection in such a way that the eluted solvent is collected in individual separated fractions. This may take place for example with a fraction collector. In this way, the high-purity RNA-containing fractions may be separated from other RNA-containing fractions which still contain undesired impurities, albeit in very small quantities. The individual fractions may be collected for example over 1 minute.

The purification by HPLC is preferably performed under completely denaturing conditions. This may proceed for example in that sample application takes place at a temperature of 4-12° C., the HPLC method otherwise proceeding at a higher temperature, preferably at 70° C. or more, particularly preferably at 75° C. or more, in particular up to 82° C., and very particularly preferably at about 78° C.

Sample application may be performed with two methods, stop-flow injection or loop injection. For stop-flow injection a microsyringe is used which is able to withstand the high pressure applied in HPLC. The sample is injected through a septum in an inlet valve either directly onto the column packing or onto a small drop of inert material immediately over the packing. The system may in this case be under elevated pressure, or the pump may be turned off prior to injection, which is then performed when the pressure has fallen to close to the normal value. In the case of loop injection, a loop injector is used to introduce the sample. This consists of a tubular loop, into which the sample is inserted. By means of a suitable rotary valve, the stationary phase is then conveyed out of the pump through the loop, whose outlet leads directly into the column. The sample is entrained in this way by the stationary phase into the column, without solvent flow to the pump being interrupted.

In an embodiment the complete hydrolysis of step b) is chemical hydrolysis. In an embodiment, the chemical hydrolysis is acid-catalyzed hydrolysis which may be accomplished by treatment of the RNA molecules with trifluoroacetic acid or with HCl at a temperature of 100° C. In another embodiment, the chemical hydrolysis is alkaline hydrolysis. For alkaline hydrolysis the pH of the RNA solution is increased, e.g. to about pH 9, preferably by the addition of an alkaline hydrolysis buffer which may contain sodium carbonate (e.g. 50 mM $NaHCO_3$/$Na_2CO_3$, pH 9.2, 1 mM EDTA) and heated to a temperature of about 95° C. for a suitable time.

In a preferred embodiment, the complete hydrolysis of step b) is enzymatic hydrolysis. In a preferred embodiment, the enzymatic hydrolysis is achieved by treatment with a nuclease, a phosphatase and a phosphodiesterase. In a more preferred embodiment, the nuclease is Nuclease P1 from *Penicillium citrinum*. In another more preferred embodiment, the phosphodiesterase is Phosphodiesterase I from *Crotalus adamanteus*. In another more preferred embodiment, the phosphatase is shrimp alkaline phosphatase. In a more preferred embodiment, the nuclease is Nuclease P1 from *Penicillium citrinum* and the phosphodiesterase is Phosphodiesterase I from *Crotalus adamanteus*. In another more preferred embodiment, the nuclease is Nuclease P1 from *Penicillium citrinum* and the phosphatase is shrimp alkaline phosphatase. In another more preferred embodiment, the phosphodiesterase is Phosphodiesterase I from *Crotalus adamanteus* and the phosphatase is shrimp alkaline phosphatase. In a most preferred embodiment, the nuclease is Nuclease P1 from *Penicillium citrinum*, the phosphodiesterase is Phosphodiesterase I from *Crotalus adamanteus* and the phosphatase is shrimp alkaline phosphatase.

In said embodiment, the RNA molecules are first hydrolyzed with nuclease P1, before phosphodiesterase I and shrimp alkaline phosphatase are added to the mixture. Preferably, the treatment with nuclease P1 is for one to three, preferably for two hours and the treatment with phosphodiesterase I and shrimp alkaline phosphatase takes place for another one to three, preferably for two hours. The temperature for treatment with nuclease P1 is preferably 42° C. and the temperature for the treatment with phosphodiesterase I and shrimp alkaline phosphatase is preferably 37° C. Preferably, 0.001 μg to 0.01 mg nuclease P1 is used per μg RNA, more preferably, 0.002 μg to 0.008 μg nuclease P1 is used per μg RNA, even more preferably 0.004 μg to 0.006 μg nuclease P1 is used per μg RNA and most preferably 0.005 μg nuclease P1 is used per μg RNA. Preferably, 0.000005 U to 0.00008 U phosphodiesterase I is used per μg RNA, more preferably 0.000008 U to 0.00006 U phosphodiesterase I is used per μg RNA, even more preferably 0.00001 U to 0.00004 U phosphodiesterase I is used per μg RNA and most preferably 0.0000217 U phosphodiesterase I is used per μg RNA. Preferably, 0.05 U to 0.5 U shrimp alkaline phosphatase is used per μg RNA, more preferably 0.08 U to 0.3 U shrimp alkaline phosphatase is used per μg RNA, even more preferably 0.1 to 0.2 U shrimp alkaline phosphatase is used per µg RNA and most preferably 0.167 U shrimp alkaline phosphatase is used per µg RNA.

Most preferably, the sample comprising RNA molecules is first treated with 0.005 µg nuclease P1 per µg RNA in a solution containing 33 mM ammonium acetate buffer pH 5.3 supplemented with 2.2 mM $ZnCl_2$ for two hours at 42° C., and then hydrolyzed with 0.0000217 U phosphodiesterase I per µg RNA and 0.167 U shrimp alkaline phosphatase per µg RNA for two more hours at 37° C. in Tris-HCl buffer pH 8.3 with 11.5 mM magnesium acetate.

After the hydrolysis step the sample comprises a mixture of all nucleosides present in the RNA molecule which was subjected to hydrolysis. To detect and optionally quantify a specific nucleoside, the nucleosides present in the mixture have to be separated from each other so that it is possible to distinguish between the nucleosides.

The skilled person knows several methods for separating and analyzing nucleosides. These methods include HPLC, eletrophoretic methods such as high-performance capillary electrophoresis (see, e.g., Cohen et al. (1987) Analytical chemistry 59(7): 1021-1027.); Matrix Assisted Laser Desorption/Ionization-Time of Flight Mass Spectrometry (MALDI-TOF MS; see, e.g., Kammerer et al. (2005) Journal of the American Society for Mass Spectrometry 16(6): 940-947); Liquid chromatography-mass spectrometry (LC-MS); chromatographic methods other than HPLC, such as hydrophilic interaction chromatography (Johnsen et al. (2011) Journal of chromatography A 1218(35): 5981-5986) and colorimetric methods using dyes which specifically bind to nucleosides or enzymes which specifically cleave nucleosides. Preferably, HPLC is used to separate the nucleosides.

If HPLC is used to separate the nucleosides, in general, any material known to be used as reverse phase stationary phase, in particular any polymeric material may be used, if that material can be provided in porous or monolithic form. The stationary phase may be composed of organic and/or inorganic material. Examples for polymers to be used for the purification step of the present invention are (non-alkylated) polystyrenes, (non-alkylated) polystyrenedivinylbenzenes, silica gel, silica gel modified with non-polar residues, particularly silica gel modified with alkyl containing residues, more preferably with butyl-, octyl and/or octadecyl containing residues, silica gel modified with phenylic residues, polymethacrylates, etc.

In a particularly preferred embodiment, the material for the reversed phase is a porous polystyrene polymer, a (non-alkylated) porous polystyrenedivinylbenzene polymer, porous silica gel, porous silica gel modified with non-polar residues, particularly porous silica gel modified with alkyl containing residues, more preferably with butyl-, octyl and/ or octadecyl containing residues, porous silica gel modified with phenylic residues, porous polymethacrylates, wherein in particular a porous polystyrene polymer or a non-alkylated (porous) polystyrenedivinylbenzene may be used.

An octadecyl capped, porous silica gel column which is very particularly preferred for the separation and detection of the nucleosides is one which, without being limited thereto, may have a particle size of 10-50 µm, particularly 10 µm and a pore size of 120-300 Å, particularly 300 Å.

The stationary phase is conventionally located in a column. V2A steel is conventionally used as the material for the column, but other materials may also be used for the column provided they are suitable for the conditions prevailing during HPLC. Conventionally the column is straight. It is favorable for the HPLC column to have a length of 5 cm to 100 cm and a diameter of 4 mm to 25 mm. Columns used for step c) of the method of the invention may in particular have the following dimensions: 250 mm long and 4.6 mm in diameter.

In a preferred embodiment, the nucleosides are applied to the HPLC column in an aqueous solvent, preferably a buffer. Preferably, the buffer used as the aqueous solvent has a pH of 5.0-7.0, more preferably of 5.5 to 6.5 and most preferably of 6.0. More preferably the buffer is ammonium acetate which preferably has a concentration of 0.001 M to 0.01 M, more preferably of 0.002 M to 0.007 M. Most preferably, a 0.005 M ammonium acetate buffer pH 6.0 is used.

In a preferred embodiment, the organic solvent which is used for eluting the nucleosides is selected from acetonitrile, methanol, ethanol, 1-propanol, 2-propanol and acetone or a mixture thereof. More preferably, the organic solvent is acetonitrile. Most preferably, it is 40 vol. % acetonitrile.

Elution may proceed isocratically or by means of gradient separation. In isocratic separation, elution of the RNA proceeds with a single eluent or a constant mixture of a plurality of eluents, wherein the solvents described above in detail may be used as eluent.

In a preferred embodiment, gradient separation is performed wherein the composition of the eluent is varied by means of a gradient program. The equipment necessary for gradient separation is known to a person skilled in the art. Gradient elution may here proceed either on the low pressure side by mixing chambers or on the high pressure side by further pumps.

Preferably, the proportion of organic solvent, as described above, is increased relative to the aqueous solvent during gradient separation. The above-described agents may here be used as the aqueous solvent and the likewise above-described agents may be used as the organic solvent. For example, the proportion of organic solvent in the mobile phase, preferably of acetonitrile, may be increased in the course of HPLC separation from 0.0 vol. % to 20.0 vol. %, in each case relative to the mobile phase.

The following gradient program has proven particularly favorable for the separation of nucleosides:

Eluent A: 0.005 M ammonium acetate, pH 6
Eluent B: 0.005 M ammonium acetate, pH 6, 40 vol. % acetonitrile
Eluent Composition:
start: 100% A and 0% B
increase to 20% B (over 50 minutes with flowrate 0.85 ml/min)

It is preferred to use purified solvent for HPLC. Such purified solvents are commercially obtainable. They may additionally also be filtered through a 1 to 5 µm microfilter, which is generally mounted in the system upstream of the pump. It is additionally preferred for all the solvents to be degassed prior to use, since otherwise gas bubbles occur in most pumps. If air bubbles occur in the solvent, they may interfere not only with separation but also with the continuous monitoring of outflow in the detector. The solvents may be degassed by heating, by vigorous stirring with a magnetic stirrer, by brief evacuation, by ultrasonication or by passing a small stream of helium through the solvent storage vessel.

The flow rate of the eluent is selected such that good separation of the nucleosides contained in the sample to be investigated takes place. The eluent flow rate may amount to from 0.5 ml/min to 5 milliliters per minute, in particular about 0.6 to 2 ml/min, more preferably 0.7 ml to 10 ml/min, even more preferably 0.85 ml/min. This flow rate may be established and regulated by the pump.

Detection proceeds preferably with a UV detector at 254 nm, wherein a reference measurement may be made at 600 nm. However, any other detection method may alternatively be used, with which the nucleosides may be detected.

Sample application may be performed with two methods, stop-flow injection or loop injection. For stop-flow injection a microsyringe is used which is able to withstand the high pressure applied in HPLC. The sample is injected through a septum in an inlet valve either directly onto the column packing or onto a small drop of inert material immediately over the packing. The system may in this case be under elevated pressure, or the pump may be turned off prior to injection, which is then performed when the pressure has fallen to close to the normal value. In the case of loop injection, a loop injector is used to introduce the sample. This consists of a tubular loop, into which the sample is inserted. By means of a suitable rotary valve, the stationary phase is then conveyed out of the pump through the loop, whose outlet leads directly into the column. The sample is entrained in this way by the stationary phase into the column, without solvent flow to the pump being interrupted.

In an embodiment, detecting the released nucleosides comprises identifying the released nucleosides by comparison to a standard for each nucleoside. In an embodiment, this standard is obtained by completely hydrolyzing the corresponding nucleoside triphosphate and detecting the resulting nucleosides by HPLC.

The corresponding nucleoside triphosphate is treated in the same way as the sample comprising RNA molecules, i.e. if the sample comprising RNA molecules is enzymatically hydrolyzed as described above, the corresponding nucleoside triphosphate is treated with the same enzymes and under the same conditions. If the sample comprising RNA molecules is subjected to chemical hydrolysis, the corresponding nucleoside triphosphate is also subjected to chemical hydrolysis.

In an embodiment, step c) of the inventive method further comprises a step c1) of quantifying the released nucleosides. In a preferred embodiment, the released nucleosides are quantified by determining the peak area for each of the nucleosides and using the linear standard plot method (Li et al. (2012) Fitoterapia 83:1267-1274). For this purpose, a linear standard curve is created by completely hydrolyzing nucleotides into nucleosides, diluting 500 µM of the relevant nucleoside 1:1 ten times, subjecting these dilutions to HPLC analysis as described above, and plotting the values of the peak areas against the concentration to create a linear standard curve.

In one embodiment, the RNA molecules are polyadenylated and step d) of the inventive method comprises determining the number of copies of the RNA molecules (n(RNA)) in the sample by using formula 1.1:

$$n(RNA)=\tfrac{1}{3}*(n(C)/u(C)+n(G)/u(G)+n(U)/u(U)),$$

wherein n(C), n(U), and n(G) is the measured content of the corresponding nucleoside and any modifications thereof in the sample, and u(C), u(U) and u(G) is the number of the corresponding nucleoside and any modifications thereof in the expected sequence of the RNA molecules. The obtained number will be the amount of RNA molecules in the sample. A is omitted from the formula since polyadenylation (addition of homopolymeric A-nucleotide element) would skew the calculation toward a higher number.

Analogously, for any other RNA molecules comprising homopolymeric elements (for example a poly(C) stretch) formula 1.1 has to be adapted accordingly (for example: $n(RNA)=\tfrac{1}{3}*(n(A)/u(A)+n(G)/u(G)+n(U)/u(U)$ if the RNA molecules comprise a poly(C) stretch).

In another embodiment, the RNA molecules are not polyadenylated and step d) of the inventive method comprises determining the number of copies of the RNA (n(RNA)) molecules in the sample by using formula 1.2:

$$n(RNA)=\tfrac{1}{4}*(n(C)/u(C)+n(G)/u(G)+n(U)/u(U)+n(A)/u(A)),$$

wherein n(C), n(U), n(G) and n(A) is the measured content of the corresponding nucleoside and any modifications thereof in the sample, and u(C), u(U) and u(G) is the number of the corresponding nucleoside and any modifications thereof in the expected sequence of the RNA molecules. The obtained number will be the amount of RNA molecules in the sample.

In an embodiment, step d) of the inventive method comprises determining the matching of the sequence of the RNA molecules with that of the known sequence and/or the matching of the length of the RNA molecules with the known length by comparing the measured ratio of a specific nucleoside in the sample (rm) with the expected ratio of said nucleoside (re).

In a preferred embodiment, the measured ratio of a specific nucleoside in the sample comprising polyadenylated RNA is determined using formula 2.1:

$$rm(X)=n(X)/[n(C)+n(G)+n(U)]$$

and the expected ratio of said nucleoside is determined using formula 3.1:

$$re(X)=u(X)/[u(C)+u(G)+u(U)],$$

wherein rm is the measured ratio of a specific nucleoside in the sample, re is the expected ratio of the corresponding nucleoside in the RNA molecules, n is the measured content of the corresponding nucleoside and any modifications thereof in the sample, u is the number of the corresponding nucleoside and any modifications thereof in the expected sequence of the RNA molecules, and X is a nucleotide selected from C, G or U, and wherein the RNA molecules are polyadenylated. The nucleoside X is the same in both formulas 2.1 and 3.1, e.g. if the rm(X) is calculated for C, the re(X) is also calculated for C.

Analogously, for any RNA molecules comprising homopolymeric elements other than a poly(A) tail (for example a poly(C) stretch) formula 2.1 has to be adapted accordingly (for example: $rm(X)=n(X)/[n(A)+n(G)+n(U)]$ if the RNA molecules comprise a poly(C) stretch) and formula 3.1 has to be adapted accordingly ($re(X)=u(X)/[u(A)+u(G)+u(U)]$ if the RNA molecules comprise a poly(C) stretch).

In one embodiment, the measured and expected ratio is calculated for each of C, G, and U in polyadenylated RNA molecules.

Analogously, for any RNA molecules comprising homopolymeric elements other than a poly(A) tail (for example a poly(C) stretch) the measured and expected ratio is calculated for each of A, G, and U in poly(C) stretch containing RNA molecules.

The obtained values for rm(X) and re(X) can then be compared. In this respect, it is to be understood that the values of the measured and expected ratio for the same nucleoside are compared. A close match between the measured and expected ratio indicates that both the sequence and the length of the RNA molecules closely match with the expected sequence and length. A low match between the measured and expected ratio could indicate that the sequence of the RNA molecules does not match with the expected sequence, e.g. that the produced RNA molecules are not the desired ones, or that transcription errors occurred, or that the RNA molecules have a different length as the expected length, e.g. that transcription did not proceed to completion or that the RNA was (partially) degraded after transcription.

In another preferred embodiment, the measured ratio of a specific nucleoside in the sample comprising non-polyadenylated RNA is determined using formula 2.2:

$$rm(X)=n(X)/[n(C)+n(G)+n(U)+n(A)]$$

and the expected ratio of said nucleoside is determined using formula 3.2:

$$re(X)=u(X)/[u(C)+u(G)+u(U)+n(A)],$$

wherein rm is the measured ratio of a specific nucleoside in the sample, re is the expected ratio of the corresponding nucleoside in the RNA molecules, n is the measured content of the corresponding nucleoside and any modifications thereof in the sample, u is the number of the corresponding nucleoside and any modifications thereof in the expected sequence of the RNA molecules, and X is a nucleotide selected from C, G, U or A, and wherein the RNA molecules is not polyadenylated. The nucleoside X is the same in both formulas 2.1 and 3.1, e.g. if the rm(X) is calculated for C, the re(X) is also calculated for C.

In one embodiment, the ratio is calculated for each of C, G, U and A in a non-polyadenylated RNA molecule.

The obtained values for rm(X) and re(X) can then be compared. In this respect, it is to be understood that the values of the measured and expected ratio for the same nucleoside are compared. In an embodiment, a low match between the measured and expected ratio could indicate that the sequence of the RNA molecules does not match with the expected sequence, e.g. that the produced RNA molecules are not the desired ones, or that transcription errors occurred, or that the length of the RNA molecules does not match with the expected length, e.g. that transcription did not proceed to completion or that the RNA was (partially) degraded after transcription.

In an embodiment, step d) of the inventive method comprises determining the capping degree of the RNA molecules by using formula 4:

$$\% \ cap=n(CA)/n(RNA)*100\%,$$

wherein % cap is the percentage of capped RNA molecules, n(CA) is the content of a cap analogue in the sample, and n(RNA) is the number of copies of the RNA molecules in the sample. A high % cap value indicates that a high percentage of RNA molecules within the sample contain a cap structure.

In a preferred embodiment, the cap analogue is selected from the group consisting of:

G[5']ppp[5' ]G, m7G[5']ppp[5]G, m32,2,7G[5]ppp[5]G, m27,3'-0G[5]ppp[5]G (3'-ARCA), m27,2'-OGpppG (2'-ARCA), m27,2'-OGppspG D1 (β-S-ARCA D1) and m27, 2'-OGppspG D2 (β-S-ARCA D2). In a preferred embodiment, the number of copies of the RNA molecules in the sample is determined using formula 1.1 if the RNA molecules are polyadenylated, or using formula 1.2 if the RNA molecules are not polyadenylated.

In another preferred embodiment, the RNA is capped using enzymatic capping.

In an embodiment, step d) of the inventive method comprises determining the length of a homopolymeric element in the RNA molecules by using formula 5:

$$l_xm=n(X)/n(RNA)-[u(X)-l_xe],$$

wherein $l_xm$ is the calculated average length of the poly(X) stretch, n(X) is the measured content of a nucleoside X forming the homopolymeric element in the sample, n(RNA) is the number of copies of the RNA molecules in the sample, u(X) is the number of X in the expected sequence of the RNA molecules, and $l_xe$ is the expected average length of the poly(X) stretch in the RNA molecules.

In a preferred embodiment, the homopolymeric element is a poly(A) stretch in the RNA molecules and the length of the poly (A) stretch is determined by using formula 5.1:

$$l_Am=n(A)/n(RNA)-[u(A)-l_Ae];$$

wherein $l_Am$ is the determined average length of the poly(A) tail, n(A) is the measured content of the nucleoside A in the sample, n(RNA) is the number of copies of the RNA molecules in the sample, u(A) is the number of nucleoside A in the expected sequence of the RNA molecules, and $l_Ae$ is the expected average length of the poly(A) stretch in the RNA molecules.

In another embodiment, the homopolymeric element is a poly(C) stretch in the RNA molecules and the length of the poly (C) stretch is determined by using formula 5.2:

$$l_Cm=n(C)/n(RNA)-[u(C)-l_Ce];$$

wherein $l_Cm$ is the determined average length of the poly(C) stretch, n(C) is the measured content of the nucleoside C in the sample, n(RNA) is the number of copies of the RNA molecules in the sample, u(C) is the number of nucleoside C in the expected sequence of the RNA molecules, and $l_Ce$ is the expected average length of the poly(C) stretch in the RNA molecules.

In either of these embodiments, the number of copies of the RNA molecules in the sample may be determined by using formula 1.1.

In an embodiment, step d) of the inventive method comprises determining the incorporation and amount of modified nucleosides into the RNA molecules by using formula 6:

$$\% \ mN=n(mN)/[n(uN)+n(mN)]*100\%,$$

wherein % mN is the percent incorporation of a modified nucleoside in the RNA molecules, n(mN) is the measured content of the modified nucleoside in the RNA molecules, and n(uN) is the measured content of the unmodified nucleoside in the RNA molecules.

In an embodiment, the modified nucleoside is selected from the group of: 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine- 5'-triphosphate, pseudouridine-5'-triphosphate, or puromycin-5'-triphosphate, xanthosine-5'-triphosphate, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethyl-guanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In one embodiment, the modified nucleosides are oxidized nucleosides so that the percentage of their incorporation into the RNA molecules allows to determine the oxidation status of the RNA molecules. The oxidized nucleosides are preferably selected from the group consisting of: 8-hydroxyguanosine (8-OHG), 8-oxo-7,8-dihydro-2'-deoxyguanosine, dehydroguanidinohyantoin, 2,4,6-trioxo-[1,3,5]triazinane-1-carboxamidine, N-nitro-dehydroguanidinohydantoin, spiroiminodihydantoin, guanidinohydantoin, 4-hydroxy-2,5-dioxo-imidazolidine-4-carboxylic acid, 3-nitrotyrosine, 3.3'-dityrosine, 3-hydroxy-5-imino-3,3a,4,5-tetrahydro-1H-imidazo[4,5-d]imidazol-2-one, parabanic acid, cyanuric acid, 4-hydroxy-8-oxo-4,8-dihydro-2'-desoxyguanosine, 4,5-dihydro-5-hydroxy-4-(nitrosooxy)-2-desoxyguanosine, 2-amino-5[(2-deoxy-β-D-erythro-pentofuranpsyl)amino]-4H-imidazol-4-one, 2,2-diamino-4-[(2-deoxy-β-D-erythro-pentofuranpsyl)amino]-5-(2H)-oxazolone, 5-[hydroxymethyl]-uracil, 2-thiobarbituric acid, 8-nitroguanine, hypoxanthine, uracil, thymine and xanthine.

In an embodiment, the RNA molecules to be analyzed are selected from the group consisting of: messenger RNA (mRNA), a viral RNA, retroviral RNA and replicon RNA, small interfering RNA (siRNA), antisense RNA (asRNA), circular RNA(circRNA), CRISPR/Cas9 guide RNA, ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA).

In a preferred embodiment, the RNA molecules being analyzed are mRNA molecules.

In an embodiment, the inventive method additionally comprises a step a.1) of modifying the RNA molecules.

In one embodiment, modifying the RNA molecules, preferably mRNA molecules, comprises enzymatically adding a poly(A) tail to the RNA molecules. This is achieved by reacting the RNA molecules with poly(A)polymerase using 1 mM ATP at 37° C. for 5 to 120 minutes, depending on the desired poly (A) tail length, preferably for 30 to 60 minutes. Preferably, the poly(A)polymerase is derived from *Escherichia coli, Streptomyces coelicolor, Meiothermus silvanus, Bacillus subtilis, Thermus aquaticus, Shigella flexneri, Shigella dysenteriae, Citrobacter koseri, Salmonella bongori, Salmonella enterica, Trabulsiella guamensis, Kluyvera ascorbata, Citrobacter freundii, Enterobacter cloacae, Enterococcus gallinarum, Grimontia indica*, or *Salinivibrio costicola*, most preferably from *Escherichia coli*.

In a preferred embodiment, the length of the enzymatically added poly(A) stretch of the RNA molecules is determined by using formula 5.1:

$$l_Am=n(A)/n(RNA)-[u(A)-l_Ae],$$

wherein $l_Am$ is the calculated average length of the poly(A) stretch, n(A) is the measured content of the nucleoside A in the sample, n(RNA) is the number of copies of the RNA molecules in the sample, u(A) is the number of nucleoside A in the expected sequence of the RNA molecules, and $l_Ae$ is the expected average length of the poly(A) stretch in the RNA molecules.

In a further preferred embodiment, the number of copies of the RNA molecules in the sample is determined using formula 1.1.

In another embodiment, modifying the RNA molecules, preferably mRNA molecules, comprises enzymatically adding a cap structure to the RNA molecules. Enzymatic capping occurs post-transcriptionally and uses a eukaryotic or viral capping enzyme, more preferably a Vaccinia virus caping enzyme (to generate cap0), still more preferably a Vaccinia virus capping enzyme and a Vaccinia virus cap-specific nucleoside 2'-O-methyltransferase (to generate cap1). The RNA molecules are reacted with the capping enzyme, a nucleotide, GTP, and a methyl donor, preferably S-adenosylmethionine. The capping reaction occurs at 25° C. for 1 hour, using for example 0.5 mg/ml RNA, 5 M nucleotide, GTP, and 1 M methyl donor, preferably S-adenosylmethionine.

In another embodiment, modifying the RNA molecules, preferably mRNA molecules, comprises enzymatically adding a cap1 structure to an RNA comprising a cap0 structure. Preferably, Vaccinia virus cap-specific nucleoside 2'-O-methyltransferase is used under suitable conditions (as explained above).

In a preferred embodiment, the incorporation of the enzymatically added cap structure into the RNA molecules is determined by using formula 4:

$$\% \text{ cap}=n(CA)/n(RNA)*100\%,$$

wherein % cap is the percentage of capped RNA molecules, n(CA) is the content of a cap structure in the sample, and n(RNA) is the number of copies of the RNA molecules in the sample. In a further preferred embodiment, the number of copies of the RNA molecules in the sample is determined using formula 1.1, if the RNA molecules are polyadenylated, or using formula 1.2, if the RNA molecules are not polyadenylated.

In an embodiment, the inventive method is used in the quality control of RNA prepared by RNA in vitro transcription. In an embodiment, the inventive method is used in the quality control of RNA prepared by chemical synthesis. Such a quality control involves determining the number of copies, matching of the sequence with the expected sequence, matching of the length with the expected length, purity and other aspects of the RNA molecules, and is particularly important in the production of RNA which is to be used for administration to humans or animals, for example for therapeutic purposes. If the sample comprising RNA molecules shows the required quality in terms of number of copies, matching of the sequence with the expected sequence, matching of the length with the expected length, and homopolymeric elements, in the case of mRNA molecules in terms of number of copies, matching of the sequence with the expected sequence, matching of the length with the expected length, poly(A) tail, and capping, and optionally for RNA or mRNA molecules incorporation of modified nucleotides and oxidation status, the sample can be processed further to be ultimately administered to a human or animal subject. If any of the criteria above are not met, the sample comprising RNA molecules will be discarded, as it is not suitable for administration to humans or animals.

EXAMPLES

The Examples shown in the following are merely illustrative and shall describe the present invention in a further way. These Examples shall not be construed to limit the present invention thereto.

Example 1: Preparation of the mRNA

1. Preparation of DNA and mRNA Constructs

For the present example, DNA sequences encoding mRNA of *Photinus pyralis* luciferase (PpLuc, R2988), three human cancer antigens (HsPSCA, R1871; HsNY-ESO-1, R1857; Hs5T4, R1855) and Rabies virus glycoprotein (RAV-G, R1803) were generated. The DNA sequences were prepared by modifying the wild type encoding DNA sequence to optimize the GC-content for stabilization. The DNA sequence was introduced into a pUC19 derived vector and modified to comprise an alpha-globin-3'-UTR (muag (mutated alpha-globin-3'-UTR)), a histone-stem-loop structure, and a stretch of 70×adenosine at the 3'-terminal end (poly-A-tail). The obtained plasmid DNA was used for RNA in vitro transcription experiments to obtain respective mRNA (SEQ ID NO. 1-5).

2. RNA In Vitro Transcription

The DNA plasmids prepared according to paragraph 1 were transcribed in vitro using T7 polymerase. All mRNAs were capped by co-transcriptional capping, using a cap analogue. In addition to that, for the preparation of PpLuc mRNA (SEQ ID No. 1), a modified nucleotide 8-OH-G was incorporated (detailed description see below).

Linearized plasmid DNA template (50 µg/ml) was transcribed at 37° C. for 3-5 hours in 80 mM HEPES/KOH, pH 7.5, 24 mM $MgCl_2$, 2 mM spermidine, 40 mM DTT, 5 U/ml pyrophosphatase (Thermo Fisher Scientific), 200 U/ml RiboLock RNase inhibitor (Thermo Fisher Scientific), 5000 U/ml T7 RNA polymerase (Thermo Fisher Scientific). Transcription was carried out in 5.8 mM m7G(5')ppp(5')G Cap Analogue, 4 mM ATP, 4 mM CTP, 4 mM UTP, and 1.45 mM GTP (all Thermo Fisher Scientific) unless otherwise stated. Following RNA in vitro transcription, linear DNA templates were removed by DNaseI (Roche) (100 U/ml, 1 mM $CaCl_2$, 1 hour at 37° C.).

In addition to PpLuc mRNA containing naturally only occurring nucleotides, an PpLuc mRNA was synthetized comprising the modified nucleotide 8-OH-G. To prepare PpLuc mRNA containing 8-OH-G ("PpLuc (8-OH-G)"), 25% of the amount of GTP applied in the RNA in vitro transcription reaction was replaced with 8-OH-GTP. The respective NTP composition used for the in vitro transcription of PpLuc (8-OH-G) was 1.025 mM 8-OH-GTP, 3.075 mM GTP, 4.36 mM CTP, 3.07 mM ATP, 1.92 mM UTP, 16.4 mM m7G(5')ppp(5')G Cap.

RNAs were precipitated in 2.86 M LiCl for 16 hours at −20° C., followed by centrifugation (30 min, 16.000 g, 4° C.). Pellets were washed in 0.1 transcription reaction volumes of 75% ethanol (invert, centrifuge 5 min, 16.000 g, 4° C.), dried and re-dissolved in 10 transcription reaction volumes $H_2O$.

3. Purification of the In Vitro Transcribed mRNA

Subsequently the mRNA was purified using PureMessenger® (see WO 2008/077592A1). PpLuc (8-OH-G) mRNA was purified with RNeasy columns (Qiagen) according to the manufacturer's instructions. The expected sequences are provided (SEQ ID NO. 1-5). Moreover, the expected nucleotide composition (A,G,U,C) of each synthetized mRNA is indicated (see Table 1).

TABLE 1

Target mRNAs used in the experiments

| Description (Name) | Identifier (R number) | SEQ ID NO | Nucleotide composition | | | |
|---|---|---|---|---|---|---|
| | | | A | G | U | C |
| PpLuc mRNA | R2988 | 1 | 427 | 570 | 267 | 606 |
| HsPSCA mRNA | R1871 | 2 | 154 | 150 | 80 | 205 |
| HsNY-ESO-1 mRNA | R1857 | 3 | 154 | 243 | 79 | 284 |
| RAV-G mRNA | R1803 | 4 | 388 | 510 | 266 | 628 |
| Hs5T4 mRNA | R1855 | 5 | 283 | 400 | 212 | 585 |

Example 2: Total Hydrolysis of RNA

The goal of this experiment was to enzymatically hydrolyze mRNA species obtained according to Example 1 to obtain the single nucleosides of each of the mRNA species. The obtained nucleoside mixtures were used for further analysis using HPLC (see Example 3).

Enzymatic Hydrolysis of mRNA mRNA was completely hydrolysed by the action of three types of hydrolases. Phosphodiesterase I from *Crotalus adamanteus* (SvP) and Nuclease P1 from *Penicillium citrinum* (P1) were obtained as dried powder from Sigma Aldrich. SvP was dissolved to 0.5 U/ml in 110 mM Tris-HCl buffer, pH 8.9, 100 mM NaCl, 15 mM MgCl2, 50% Glycerol and stored at −20° C. P1 was dissolved to 1 g/L in 20 mM sodium acetate buffer pH 5.3, 5 mM ZnCl2, 50 mM NaCl, 50% Glycerol and stored at −20° C. Shrimp alkaline phosphatase (AP) was obtained from New England Biolabs.

60 μg of each mRNA was hydrolysed first for 2 h at 42° C. with 0.3 μg of P1 in 33 mM ammonium acetate buffer pH 5.3 supplemented with 2.2 mM $ZnCl_2$. Second, Tris-HCl buffer (pH 8.3), magnesium acetate, SvP and AP were added to 11.5 mM, 1.15 mM, 10 U/1 or 0.077 U/μl, respectively (reaction volume: 130 μl). The hydrolysis was allowed to proceed for 2 h at 37° C. After that, the reaction was centrifuged for 10 min at 30,000 g. The supernatant was supplemented with 2.2 μl of ammonium acetate buffer pH 5.3 (300 mM). 20 μl of the resulting solution were analyzed by HPLC (see Example 3)

Example 3: HPLC Analysis of the Hydrolysed mRNA

The goal of this experiment was to analyse each nucleoside mixture obtained via total mRNA hydrolysis (see Example 2) by HPLC to gain information about the matching of the sequence with the expected sequence, the matching of the length with the expected length, the capping efficiency, the incorporation rate of modified nucleosides (8-OH-G), oxidation and the length of the poly(A) stretch of each hydrolysed mRNA.

This inventive method can be used as a multifaceted quality control of in vitro transcribed mRNA.

1. HPLC Analysis of Nucleosides

Samples obtained via total hydrolysis (see Example 2) were separated using a commercially available HPLC setup. In essence, an octadecyl capped silica column (YMC*Gel ODS-A-HG, pore size: 300 A, particle size: 10 μm, dimensions (ID×h) 250 mm×4.6 mm, YMC) in a linear gradient from 100% Buffer A (5 mM NH$_4$OAc pH 6) to 20% Buffer B (40% v/v acetonitrile) was used for the separation of nucleosides in the hydrolysate samples. In addition, nucleotide triphosphates were hydrolysed (according to Example 2) and analysed at 254 nm to obtain standards for calibration. A commercially available HPLC machine was used for the separation of hydrolysates and nucleoside standards. The nucleosides were detected at a wavelength of 254 nm. Exemplary chromatograms for a hydrolysate of PpLuc mRNA and respective standards are shown in FIG. 1.

2. Calculation of the Amount of RNAs in the Analysis

With single nucleoside standards prepared by hydrolyzing the respective triphosphates, the expected content of C, G, A, U, m7G (cap analogue) and optionally 8-OH-G in each mRNA hydrolysate sample was determined (n(C), n(G), n(A), n(U), n(m7G), n(8-OH-G)). The number of C, G, A, and U in each mRNA sequence was determined (u(C), u(G), u(A), u(U)) (see Table 1).

As the length of the poly A stretch may vary, the content of adenosine is omitted for the calculation of the amount of analyzed mRNA. Instead, the amount of mRNA in each mRNA hydrolysate was calculated with formula 1.3:

$n(RNA)=⅓*(n(C)/u(C)+[n(G)+n(8\text{-}OH\text{-}G)]/u(G)+u(8\text{-}OH\text{-}G)]+n(U)/u(U))$.

3. mRNA Identity Measurement

The obtained mRNA hydrolysates were analyzed for their nucleoside composition. This measurement can be used to reliably identify mRNA species because the measured ratio of C:G:U has to match the expected ratio of C:G:U. This measurement is particularly useful as a quality control step of in vitro transcribed mRNA for the determination of mRNA identity, i.e. whether the sequence of the RNA molecules matches with the expected sequence. Moreover, if the expected C:G:U values do not match the measured C:G:U values, it will indicate that the mRNA has a length which differs from the expected length.

To identify the respective mRNA species, for each of the nucleosides C, G and U, the measured and expected ratio (rm and re) were calculated with formulas 2.1 and 3.1:

$rm(X)=n(X)/[n(C)+n(G)+n(U)]$ where $X$ may be C, G or U    Formula 2.1:

$re(X)=u(X)/[u(C)+u(G)+u(U)]$ where $X$ may be C, G or U    Formula 3.1:

The measured ratio of nucleosides of one mRNA species was compared to the expected ratios of said mRNA species.

Figure 2:
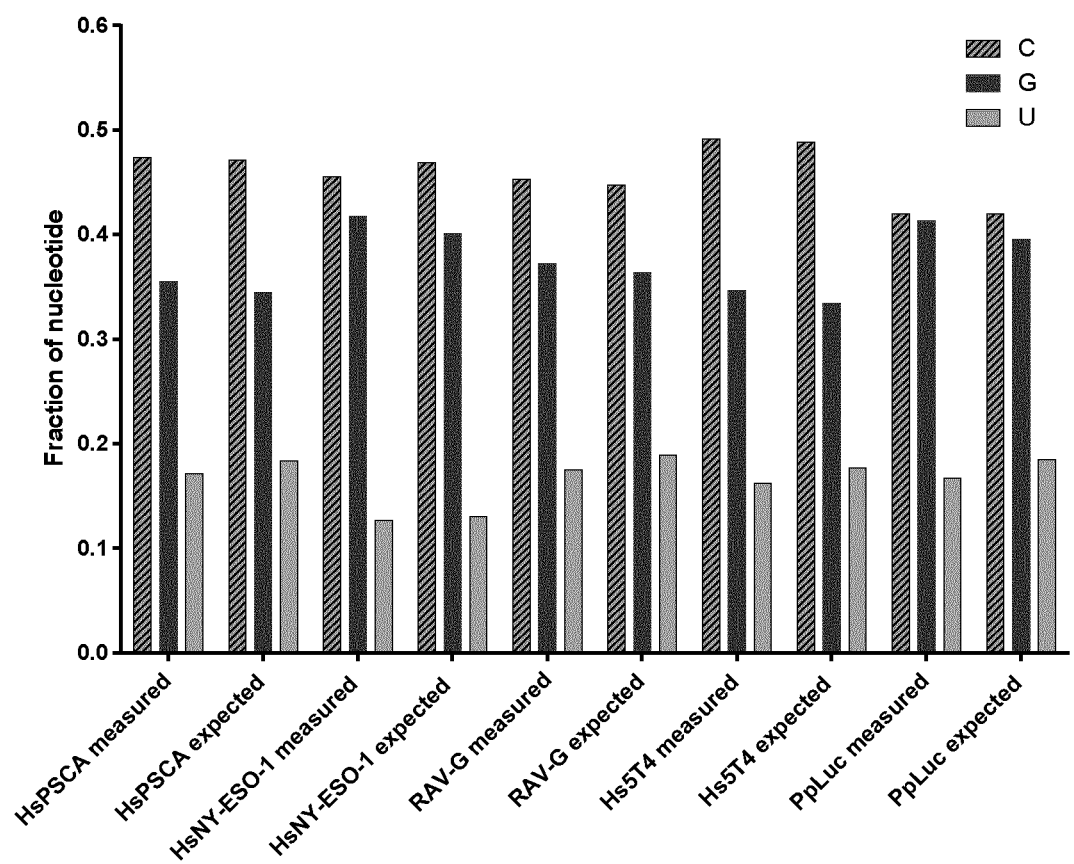
FIG. 2: shows a comparison of the measured and the expected nucleoside ratios (C:G:U) for the indicated five mRNA hydrolysates. For experimental details see Example 3.

FIG. 2 illustrates that the inventive method is particularly suitable for measuring mRNA quality attributes such as mRNA identity. The measured G:C:U ratios and the expected G:C:U ratios largely match, which shows that the method allows a robust identification of mRNA species. In addition to that, if discrepancies in the G:C:U ratios are observed, this could be an indication for a difference in the length of the RNAs. For example, abortive sequences that could potentially be produced during the process of RNA in vitro transcription may bias the measured G:C:U ratio.

4. Calculation of Incorporation of m7G into mRNA

The amount of m7G (cap analogue) from the capping structure in the mRNA hydrolysate was determined (n(CA)). As the amount of RNA in the analysis can be determined from the amount of C, G and U, the percentage of capped RNA (% cap) can also be determined in the respective samples, using Formula 4:

% cap=$n(CA)/n(RNA)*100\%$

The 5' cap of mRNA is an essential structure of protein coding mRNAs, because non-capped mRNA is not translated into protein. Therefore, determining the capping efficiency of in vitro transcribed mRNA is a key quality control of in vitro transcribed mRNA.

Figure 3:
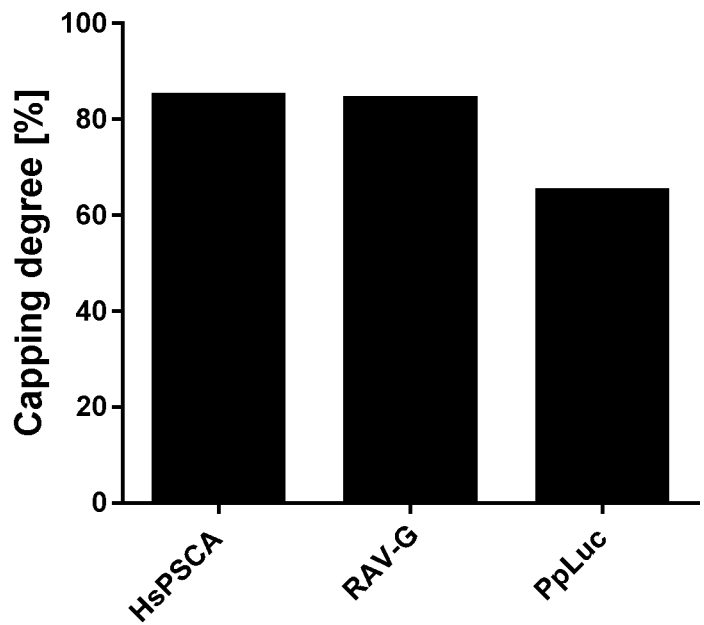
FIG. 3: shows a comparison of the capping degree calculated for the indicated three mRNA hydrolysates. For experimental details see Example 3.

FIG. 3 illustrates that the inventive method is particularly suitable for measuring mRNA quality attributes such as mRNA capping efficiency. Capping is a key feature of mRNA because non-capped mRNA is not translated into proteins.

5. Calculation of the Length of the Poly(A) Stretch in mRNA

The content of adenosines of an mRNA sample can be used to determine the length of a poly A-stretch present in the respective mRNA species (expected value: AXe). This measurement is particularly useful as a quality control step of in vitro transcribed mRNA, because plasmid encoded Poly(A) stretches can vary. A similar measurement can also be applied for mRNAs with enzymatically added Poly(A) tails (see Example 4). First, the content of A in the sequence "outside" the poly A-stretch is calculated [u(A)−AXe], which is then used to calculate the average length of the poly(A) stretch measured (AXm) (Formula 5.1):

$l_Am=n(A)/n(RNA)-[u(A)-l_Ae]$.

Figure 4:
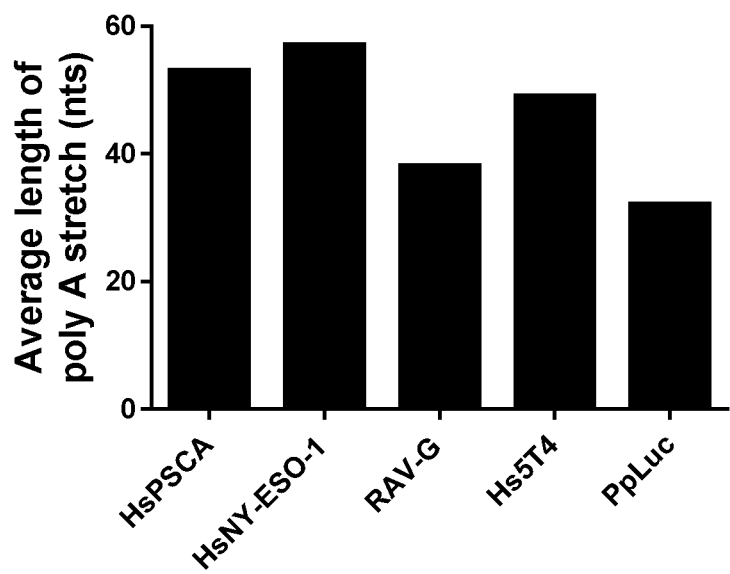
FIG. 4: shows a comparison of the length of the poly(A) stretch in the indicated five mRNA hydrolysates. For experimental details see Example 3.

FIG. 4 illustrates that the inventive method is also suitable for measuring mRNA quality attributes such as the length of the Poly(A) stretch. It is also possible to adapt the measurement in a way that other homopolymeric elements in an mRNA (e.g., a Poly(C) region) can be analyzed.

6. Calculation of the Incorporation and Amount of Modified Nucleotides

As a modified nucleotide, 8-OH-G was incorporated into the mRNA of PpLuc by replacing 25% of GTP with 8-OH-GTP during RNA in vitro transcription, yielding PpLuc(8-OH-G) (see Example 1). The ratio of incorporated 8-OH-G to incorporated G was calculated with formula 6:

$$\% \ mN = n(mN)/[n(uN)+n(mN)]*100\%$$

Figure 5:
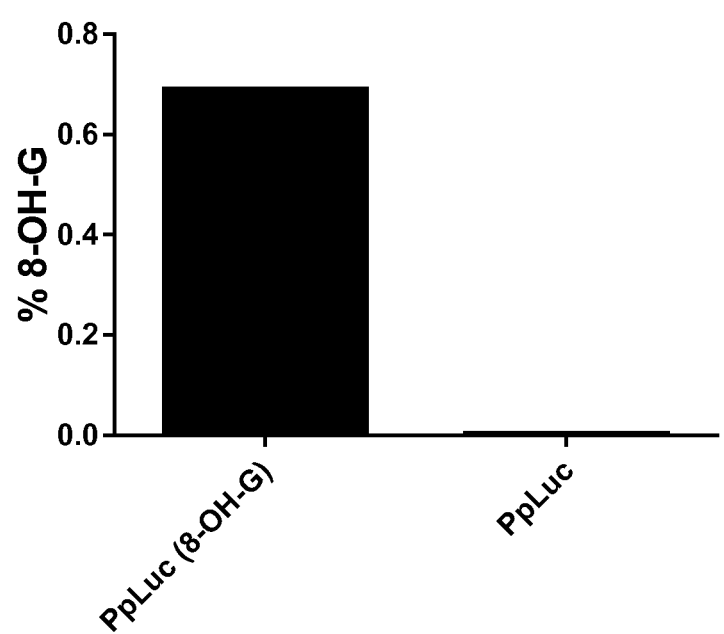
FIG. 5: shows a comparison of the frequency of 8-OH-G incorporation in PpLuc mRNA without and with 8-OH-GTP added to the respective transcription reaction ["PpLuc" and "PpLuc (8-OH-G)" respectively]. For experimental details see Example 3.

The results obtained for PpLuc (8-OH-G) were compared to the results obtained for PpLuc FIG. 5 illustrates that the inventive method is also suitable for determining the incorporation and amount of modified nucleotides. In addition, 8-OH-G is an indicator for mRNA oxidation. Therefore, the inventive method is also suitable for determining whether the produced mRNA is oxidized.

This measurement is particularly useful as a quality control of in vitro transcribed mRNA, because 8-OH-G is an indicator of mRNA oxidation. Moreover, this measurement can also be used and adapted for the detection of any modified nucleotide that may be incorporated into an mRNA, and is therefore particularly important as a quality control in the production process of mRNA containing modified nucleotides.

Summarizing the above examples, the results of the experiments show that the inventive method can be used as a multifaceted quality control for the analysis of various critical quality attributes of an in vitro transcribed mRNA.

Example 4: Preparation of Enzymatically Polyadenylated mRNA and Analysis of the Poly(A) Tail The goal of this experiment is to use the HPLC method according to Example 3 to assess the length of a poly(A) tail that has been enzymatically added. This is a crucial quality control of mRNA. In addition to that, the capping efficiency is characterized and the nucleoside composition is analyzed.

1. Enzymatic Polyadenylation:

mRNA obtained from RNA in vitro transcription according to Example 1 was polyadenylated using a conventional polyadenylation kit according to the manufacturers' instructions (Poly(A) Polymerase Tailing Kit; epicenter).

In short, mRNA is reacted with *Escherichia coli* poly(A) polymerase using 1 mM ATP at 37° C. for 30 or 60 min (dependent on the desired poly-A tail length). After polyadenylation, the mRNA is purified using PureMessenger® as described in WO 2008/077592A1. The polyadenylated and purified mRNA is optionally run on a gel to roughly assess mRNA extension.

2. HPLC Analysis of Poly(A) Tails:

The polyadenylated mRNA is first hydrolyzed (according to Example 2) and subsequently analyzed via HPLC (according to Example 3). The average length of the enzymatic polyA tail (AX) is then be calculated by formula 5.1:

$$l_A m = n(A)/n(RNA) - [u(A) - l_A e].$$

Both poly(A) tail length and capping efficiency are calculated. In addition to that, the nucleoside composition is determined for measurement of the matching of the length with the expected length and the matching of the sequence with the expected sequence.

Specific embodiments relate to:
1. Method for analyzing a sample comprising RNA molecules, comprising the steps of:
   a) providing a sample comprising RNA molecules;
   b) completely hydrolyzing the RNA molecules, thereby releasing nucleosides;
   c) separating the released nucleosides;
   d) determining at least one of:
   the content of the RNA molecules in the sample,
   the identity of the RNA molecules,
   the integrity of the RNA molecules,
   the capping degree of the RNA molecules within the sample, and
   the length of homopolymeric elements in the RNA molecules.
2. Method according embodiment 1, wherein step d) further comprises determining at least one of:
   the incorporation and amount of modified nucleotides into the RNA molecules, and
   the oxidation status of the RNA molecules.
3. Method according to any of the preceding embodiments, wherein step d) comprises determining:
   the content of the RNA molecules in the sample,
   the identity of the RNA molecules,
   the integrity of the RNA molecules,
   the capping degree of the RNA molecules within the sample,
   the length of homopolymeric elements in the RNA molecules,
   the incorporation and amount of modified nucleotides into the RNA molecules, and
   the oxidation status of the RNA molecules.
4. Method according to any one of the preceding embodiments, wherein the RNA molecules are provided by chemical synthesis.
5. Method according to any one of embodiments 1 to 3, wherein the RNA molecules are provided by in vitro transcription.
6. Method according to embodiment 5, further comprising a step a1) of purifying the RNA molecules.
7. Method according to embodiment 6, wherein step a1) comprises purifying the RNA molecules by HPLC.
8. Method according to any one of the preceding claims, wherein step b) comprises completely hydrolyzing the RNA molecules by enzyme treatment.
9. Method according to any of the preceding claims, wherein step b) comprises completely hydrolyzing the RNA molecules by treatment with a nuclease, a phosphatase and a phosphodiesterase.
10. Method according to embodiment 9, wherein the nuclease is Nuclease P1 from *Penicillium citrinum*.
11. Method according to embodiments 9 or 10, wherein the phosphodiesterase is Phosphodiesterase I from *Crotalus adamanteus*.
12. Method according to any one of embodiments 9 to 11, wherein the phosphatase is shrimp alkaline phosphatase.
13. Method according to any one of the preceding embodiments, wherein step c) comprises separating the released nucleosides by HPLC.
14. Method according to embodiment 13, wherein in the HPLC of step c) an octadecyl capped silica column is used for separating the released nucleosides.

15. Method according to embodiment 13 or 14, wherein in the HPLC a mobile phase comprising an aqueous solvent is used.
16. Method according to embodiment 15, wherein the aqueous solvent is ammonium acetate.
17. Method according to embodiment 15 or 16, wherein the aqueous solvent is 5 mM NH$_4$OAc, pH 6.
18. Method according to any one of embodiments 14 to 17, wherein the nucleosides are eluted with an organic solvent.
19. Method according to embodiment 18, wherein a linear gradient of the organic solvent is used.
20. Method according to embodiment 19, wherein the gradient is from 0% to 20% of the organic solvent.
21. Method according to any one of embodiment 18 to 20, wherein the organic solvent is 40% v/v acetonitrile.
22. Method according to any one of the preceding embodiments, wherein step c) further comprises detecting the released nucleosides and identifying the released nucleosides by comparison to a standard for each nucleoside.
23. Method according to any one of the preceding embodiments, wherein step c) further comprises a step c1) of quantifying the released nucleosides.
24. Method according to embodiment 23, wherein the released nucleosides are quantified by determining the peak area for each of the nucleosides and comparing it to a standard curve.
25. Method according to any one of the preceding embodiments, wherein the RNA molecules are polyadenylated and step d) comprises determining the content of the RNA (n(RNA)) molecules in the sample by using formula 1.1:

$$n(RNA)=\frac{1}{3}*(n(C)/u(C)+n(G)/u(G)+n(U)/u(U)),$$

wherein n(C), n(U), and n(G) is the measured content of the corresponding nucleoside and any modifications thereof in the sample, and u(C), u(U), and u(G) is the number of the corresponding nucleoside and any modifications thereof in the expected sequence of the RNA molecules.
26. Method according to any one of embodiments 1 to 24, wherein the RNA molecules are not polyadenylated and step d) comprises determining the content of the RNA (n(RNA)) molecule in the sample by using formula 1.2:

$$n(RNA)=\frac{1}{4}*(n(C)/u(C)+n(G)/u(G)+n(U)/u(U)+n(A)/u(A)),$$

wherein n(C), n(U), n(G) and n(A) is the measured content of the corresponding nucleoside and any modifications thereof in the sample, and n(C), n(U), n(G) and n(A) is the number of the corresponding nucleoside and any modifications thereof in the expected sequence of the RNA molecules.
27. Method according to any one of the preceding embodiments, wherein step d) comprises determining the identity and/or integrity of the RNA molecules by comparing the measured ratio of a specific nucleoside in the sample with the expected ratio of said nucleoside.
28. Method according to embodiment 27, wherein the RNA molecules are polyadenylated and the measured ratio of a specific nucleoside in the sample is determined using formula 2.1:

$$rm(X)=n(X)/[n(C)+n(G)+n(U)]$$

and the expected ratio of said nucleoside is determined using formula 3.1:

$$re(X)=u(X)/[u(C)+u(G)+u(U)],$$

wherein rm is the measured ratio of a specific nucleoside in the sample, re is the expected ratio of the corresponding nucleoside in the RNA molecules, n(C), n(U), and n(G) is the measured content of the corresponding nucleoside and any modifications thereof in the sample, u(C), u(U), and u(G) is the number of the corresponding nucleoside and any modifications thereof in the expected sequence of the RNA molecules, and X is a nucleotide selected from C, G and U and is the same nucleotide for both rm(X) and re(X).
29. Method according to embodiment 27, wherein the RNA molecules are not polyadenylated and the measured ratio of a specific nucleoside in the sample is determined using formula 2.2:

$$rm(X)=n(X)/[n(C)+n(G)+n(U)+n(A)]$$

and the expected ratio of said nucleoside is determined using formula 3.2:

$$re(X)=u(X)/[u(C)+u(G)+u(U)+n(A)],$$

wherein rm is the measured ratio of a specific nucleoside in the sample, re is the expected ratio of the corresponding nucleoside in the RNA molecules, n(C), n(U), n(G) and n(A) is the measured content of the corresponding nucleoside and any modifications thereof in the sample, n(C), n(U), n(G) and n(A) is the number of the corresponding nucleoside and any modifications thereof in the expected sequence of the RNA molecules, and X is a nucleotide selected from C, G, U or A.
30. Method according to any one of embodiments 27 to 29, wherein the measured and the expected ratio is determined for each of C, G, U and/or A.
31. Method according to any one of embodiments 27 to 30, wherein a mismatch between the values for rm and re indicates low identity and/or integrity of the RNA molecules.
32. Method according to any one of the preceding claims, wherein step d) comprises determining the capping degree of the RNA molecules within the sample by using formula 4:

$$\% \ cap=n(CA)/n(RNA)*100\%,$$

wherein % cap is the percentage of capped RNA molecules, n(CA) is the content of a cap analogue in the sample, and n(RNA) is the content of the RNA molecules in the sample.
33. Method according to embodiment 32, wherein the cap analogue is selected from the group consisting of: G[5']ppp[5']G, m7G[5']ppp[5']G, m32,2,7G[5']ppp[5']G, m27,3'-OG[5' ]ppp[5']G (3'-ARCA), m27,2'-OGpppG (2'-ARCA), m27,2'-OGppspG D1 (β-S-ARCA D1) and m27,2'-OGppspG D2 (β-S-ARCA D2).
34. Method according to embodiments 32 or 33, wherein the content of the RNA molecules in the sample is determined as described in embodiment 25 if the RNA molecules are polyadenylated, or as described in embodiment 26 if the RNA molecule are not polyadenylated.
35. Method according to any one of the preceding embodiments, wherein step d) comprises determining the length of a homopolymeric element in the RNA molecules by using formula 5:

$$l_xm=n(X)/n(RNA)-[u(X)-l_xe],$$

wherein $l_xm$ is the calculated average length of the poly(X) stretch, n(X) is the measured content of a nucleoside X forming the homopolymeric element in the sample, n(RNA) is the content of the RNA molecules in the sample, u(X) is the number of X in the expected sequence of the RNA molecules, $l_xe$ is the expected average length of the poly(X) stretch in the RNA molecules.

36. Method according to embodiment 35, wherein the homopolymeric element is a poly(A) stretch and wherein the length of the poly (A) stretch is determined by using formula 5.1.

$$l_Am=n(A)/n(RNA)-[u(A)-l_Ae];$$

wherein $l_Am$ is the calculated average length of the poly(A) stretch, n(A) is the measured content of the nucleoside A in the sample, n(RNA) is the content of the RNA molecules in the sample, u(A) is the number of nucleoside A in the expected sequence of the RNA molecules, and $l_Ae$ is the expected average length of the poly(A) stretch in the RNA molecules.

37. Method according to embodiment 35 or 36, wherein the content of the RNA molecules in the sample is determined as described in embodiment 25.

38. Method according to any one of embodiments 2 to 37, wherein step d) comprises determining the incorporation of modified nucleosides into the RNA molecules by using formula 6:

$$\% \ mN=n(mN)/[n(uN)+n(mN)]*100\%,$$

wherein % mN is the percent incorporation of a modified nucleoside in the RNA molecules, n(mN) is the measured content of the modified nucleoside in the RNA molecules, and n(uN) is the measured content of the unmodified nucleoside in the RNA molecules.

39. Method according to embodiment 38, wherein the modified nucleoside is selected from the group consisting of: 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudo iso cytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

40. Method according to embodiment 38, wherein the modified nucleosides are oxidized nucleosides, and wherein % mN indicates the oxidation status of the RNA molecules.

41. Method according to embodiment 40, wherein the oxidized nucleosides are selected from the group consisting of: 8-hydroxyguanosine (8-OHG), 8-oxo-7,8-dihydro-2'-deoxyguanosine, dehydroguanidinohyantoin, 2,4,6-trioxo-[1,3,5]triazinane-1-carboxamidine, N-nitro-dehydroguanidinohydantoin, spiroiminodihydantoin, guanidinohydantoin, 4-hydroxy-2,5-dioxo-imidazolidine-4-carboxylic acid, 3-nitrotyrosine, 3.3'-dityrosine, 3-hydroxy-5-imino-3,3a,4,5-tetrahydro-1H-imidazo[4,5-d]imidazol-2-one, parabanic acid, cyanuric acid, 4-hydroxy-8-oxo-4,8-dihydro-2'-desoxyguanosine, 4,5-dihydro-5-hydroxy-4-(nitrosooxy)-2-desoxyguanosine, 2-amino-5[(2-deoxy-β-D-erythro-pentofuranpsyl)amino]-4H-imidazol-4-one, 2,2-diamino-4-[(2-deoxy-β-D-erythro-pentofuranpsyl) amino]-5-(2H)-oxazolone, 5-[hydroxymethyl]-uracil, 2-thiobarbituric acid, 8-nitroguanine, hypoxanthine, uracil, thymine and xanthine.

42. Method according to any one of the preceding embodiments, wherein the RNA molecules are mRNA molecules.

43. Method according to any one of the preceding embodiments, additionally comprising step a1) of modifying the RNA molecules.

44. Method according to embodiment 43, wherein modifying the RNA molecules comprises enzymatically adding a poly(A) stretch to the RNA molecules.
45. Method according to embodiment 44, wherein step d) comprises determining the length of the enzymatically added poly(A) stretch of the RNA molecules by using formula 5.1:

$$l_A m = n(A)/n(RNA) - [u(A) - l_A e],$$

wherein $l_A m$ is the calculated average length of the poly(A) stretch, $n(A)$ is the measured content of nucleoside A in the sample, $n(RNA)$ is the content of the RNA molecules in the sample, $u(A)$ is the number of nucleoside A in the expected sequence of the RNA molecules, and $l_A e$ is the expected average length of the poly(A) stretch in the RNA molecules.

46. Method according to embodiment 45, wherein the content of the RNA molecules in the sample is determined as described in embodiment 25.
47. Method according to embodiment 43, wherein modifying the RNA molecules comprises enzymatically adding a cap structure to the RNA molecules.
48. Method according to embodiment 47, wherein the capping degree of the RNA molecules within the sample is determined by using formula 4:

$$\% cap = n(CA)/n(RNA) * 100\%,$$

wherein % cap is the percentage of the capped RNA molecules, $n(CA)$ is the content of a cap analogue in the sample, and $n(RNA)$ is the content of the RNA molecules in the sample.

49. Method according to embodiment 48, wherein the content of the RNA molecules in the sample is determined as described in embodiment 25 if the RNA molecules are polyadenylated, or as described in embodiment 26 if the RNA molecules are not polyadenylated.
50. Method according to embodiment 43, wherein modifying the RNA molecules comprises enzymatically modifying the nucleotides of the RNA molecules.
51. Method according to embodiment 50, wherein the percentage of enzymatically modified nucleosides in the RNA molecules is determined by using formula 6:

$$\% mN = n(mN)/[n(uN) + n(mN)] * 100\%,$$

wherein % mN is the percentage of a modified nucleoside in the RNA molecules, $n(mN)$ is the measured content of the modified nucleoside in the RNA molecules, and $n(uN)$ is the measured content of the unmodified nucleoside in the RNA molecules.

52. Use of the method according to any one of embodiments 1 to 3 and 5 to 51 in the quality control of RNA prepared by RNA in vitro transcription.
53. Use of the method according to any one of embodiments 1 to 4 and 8 to 51 in the quality control of RNA prepared by chemical synthesis.

The invention claimed is:

1. A method for analyzing a sample comprising RNA molecules transcribed from a template DNA with an expected sequence and length, comprising the steps of:
   a) providing a sample comprising RNA molecules, wherein the RNA molecules comprise RNA molecules that are capped and polyadenylated;
   b) completely hydrolyzing the RNA molecules, thereby releasing nucleosides;
   c) separating and quantifying the released nucleosides by HPLC, capillary electrophoresis or mass spectrometry;
   d) determining at least one of:
      (i) the capping degree of the RNA molecules within the sample by using formula 4:

% cap=$n(CA)/n(RNA)*100\%$, wherein % cap is the percentage of capped RNA molecules, n(CA) is the content of a cap analogue in the sample, and n(RNA) is the number of copies of the RNA molecules in the sample;

(ii) the number of copies of the RNA (n(RNA)) molecules in the sample by using formula 1.1:

$$n(RNA)=\frac{1}{3}*(n(C)/u(C)+n(G)/u(G)+n(U)/u(U)),$$

wherein n(C), n(U), and n(G) is the measured content of the corresponding nucleoside and any modifications thereof in the sample, and u(C), u(U), and u(G) is the number of the corresponding nucleoside and any modifications thereof in the expected sequence of the RNA molecules; and/or (iii) the length of a homopolymeric element in the RNA molecules by using formula 5:

$$l_xm=n(X)/n(RNA)-[u(X)-l_xe],$$

wherein $l_xm$ is the calculated average length of the poly(X) stretch, n(X) is the measured content of a nucleoside X forming the homopolymeric element in the sample, n(RNA) is the number of copies of the RNA molecules in the sample, u(X) is the number of X in the expected sequence of the RNA molecules, $l_xe$ is the expected average length of the poly(X) stretch in the RNA molecules.

2. The method of claim 1, wherein step d) further comprises determining at least one of:
the incorporation and amount of modified nucleotides into the RNA molecules, and
the oxidation status of the RNA molecules.

3. The method of claim 1, wherein step d) comprises determining:
the number of copies of the RNA molecules in the sample,
the matching of the sequence of the RNA molecules with the expected sequence,
the matching of the length of the RNA molecules with the expected length,
the capping degree of the RNA molecules within the sample,
the length of homopolymeric elements in the RNA molecules,
the incorporation and amount of modified nucleotides into the RNA molecules, and
the oxidation status of the RNA molecules.

4. The method of claim 1, further comprising transcribing the RNA molecules from a DNA template by in vitro transcription.

5. The method of claim 4, further comprising a step a1) of purifying the RNA molecules by HPLC.

6. The method of claim 1, wherein step b) comprises completely hydrolyzing the RNA molecules by treatment with a nuclease, a phosphatase, and a phosphodiesterase.

7. The method of claim 1, wherein step c) comprises separating and quantifying the released nucleosides by HPLC.

8. The method of claim 1, wherein step d) comprises determining the number of copies of the RNA (n(RNA)) molecules in the sample by using formula 1.1:

$$n(RNA)=\frac{1}{3}*(n(C)/u(C)+n(G)/u(G)+n(U)/u(U)),$$

wherein n(C), n(U), and n(G) is the measured content of the corresponding nucleoside and any modifications thereof in the sample, and u(C), u(U), and u(G) is the number of the corresponding nucleoside and any modifications thereof in the expected sequence of the RNA molecules.

9. The method of claim 1, wherein step d) comprises determining the matching of the sequence of the RNA molecules with the expected sequence and/or matching of the length of the RNA molecules with the expected length by comparing the measured ratio of a specific nucleoside in the sample with the expected ratio of said nucleoside.

10. The method of claim 9, wherein the measured ratio of a specific nucleoside in the sample is determined using formula 2.1:

$$rm(X)=n(X)/[n(C)+n(G)+n(U)]$$

and the expected ratio of said nucleoside is determined using formula 3.1:

$$re(X)=u(X)/[u(C)+u(G)+u(U)],$$

wherein rm is the measured ratio of a specific nucleoside in the sample, re is the expected ratio of the corresponding nucleoside in the RNA molecules, n(C), n(U), and n(G) is the measured content of the corresponding nucleoside and any modifications thereof in the sample, u(C), u(U), and u(G) is the number of the corresponding nucleoside and any modifications thereof in the expected sequence of the RNA molecules, and X is a nucleotide selected from C, G and U and is the same nucleotide for both rm(X) and re(X), wherein a mismatch between the values for rm and re indicates that the sequence of the RNA molecules does not match with the expected sequence and/or that the length of the RNA molecules does not match with the expected length.

11. The method of claim 1, wherein step d) comprises determining the capping degree of the RNA molecules within the sample by using formula 4:

$$\% \, cap=n(CA)/n(RNA)*100\%,$$

wherein % cap is the percentage of capped RNA molecules, n(CA) is the content of a cap analogue in the sample, and n(RNA) is the number of copies of the RNA molecules in the sample.

12. The method of claim 1, wherein step d) comprises determining the length of a homopolymeric element in the RNA molecules by using formula 5:

$$l_xm=n(X)/n(RNA)-[u(X)-l_xe],$$

wherein $l_xm$ is the calculated average length of the poly(X) stretch, n(X) is the measured content of a nucleoside X forming the homopolymeric element in the sample, n(RNA) is the number of copies of the RNA molecules in the sample, u(X) is the number of X in the expected sequence of the RNA molecules, $l_xe$ is the expected average length of the poly(X) stretch in the RNA molecules.

13. The method of claim 12, wherein the homopolymeric element is a poly(A) stretch and wherein the length of the poly (A) stretch is determined by using formula 5.1:

$$l_Am=n(A)/n(RNA)-[u(A)-l_Ae];$$

wherein $l_Am$ is the calculated average length of the poly(A) stretch, n(A) is the measured content of the nucleoside A in the sample, n(RNA) is the number of copies of the RNA molecules in the sample, u(A) is the number of nucleoside A in the expected sequence of the RNA molecules, and $l_Ae$ is the expected average length of the poly(A) stretch in the RNA molecules.

14. The method of claim 2, wherein step d) further comprises determining the incorporation of modified nucleosides into the RNA molecules by using formula 6:

$$\% \, mN=n(mN)/[n(uN)+n(mN)]*100\%,$$

wherein % mN is the percent incorporation of a modified nucleoside in the RNA molecules, n(mN) is the measured content of the modified nucleoside in the RNA molecules, and n(uN) is the measured content of the unmodified nucleoside in the RNA molecules.

15. The method of claim 14, wherein the modified nucleosides are oxidized nucleosides, and wherein % mN indicates the oxidation status of the RNA molecules.

16. The method of claim 1, wherein the RNA molecules are mRNA molecules.

17. The method of claim 1, additionally comprising step a1) of modifying the RNA molecules.

18. The method of claim 7, wherein an octadecyl capped silica column is used for separating the released nucleosides by HPLC.

19. The method of claim 1, wherein step c) comprises separating and quantifying the released nucleosides by capillary electrophoresis.

20. The method of claim 1, wherein step c) comprises separating and quantifying the released nucleosides by mass spectrometry.

\* \* \* \* \*